(12) United States Patent
Holtzman

(10) Patent No.: US 6,972,318 B1
(45) Date of Patent: Dec. 6, 2005

(54) COMPLEX OF A CHAPERONE PROTEIN WITH AMYLOID

(76) Inventor: Jordan L. Holtzman, 4710 Girard Ave. South, Minneapolis, MN (US) 55409

( * ) Notice: Subject to any disclaimer, the term of this patent is extended or adjusted under 35 U.S.C. 154(b) by 0 days.

(21) Appl. No.: 09/830,749

(22) PCT Filed: Oct. 29, 1999

(86) PCT No.: PCT/US99/25593
§ 371 (c)(1),
(2), (4) Date: Jun. 25, 2001

(87) PCT Pub. No.: WO00/26251
PCT Pub. Date: May 11, 2000

Related U.S. Application Data

(60) Provisional application No. 60/106,398, filed on Oct. 30, 1998, provisional application No. 60/123,564, filed on Mar. 10, 1999.

(51) Int. Cl.$^7$ .......................................... C07K 14/435
(52) U.S. Cl. ..................................... 530/300; 530/350
(58) Field of Search ................................ 530/350, 300

(56) References Cited

U.S. PATENT DOCUMENTS 5,780,587 A    7/1998  Potter .......................... 530/326

FOREIGN PATENT DOCUMENTS

EP    0 783 104    12/1996
WO    WO 96/12736    5/1996

OTHER PUBLICATIONS

Rudinger, In Peptide Hormones (ed. J.A. Parsons) University Park Press, Baltimore, pp. 1-7, 1976.*
Ida et al., 1996, *The Journal of Biological Chemistry*, 271:22908-22914, "Analysis of Heterogeneous βA4 Peptides in Human Cerebrospinal Fluid and Blood by a Newly Developed Sensitive Western Blot Assay".
Matsubara et al., 1996, *Biochemical Journal*, 316:671-679, "Apolipoprotein J and Alzheimer's amyloid β solubility".

* cited by examiner

*Primary Examiner*—Brenda Brumback
*Assistant Examiner*—Robert C. Hayes
(74) *Attorney, Agent, or Firm*—Merchant & Gould P.C.

(57) ABSTRACT

A chaperone protein Q2 and β-amyloid can form a complex. This complex can be detected in a biological sample, such as, for example, tissues or fluids from a mammal. Q2 levels can also be detected in a biological sample. A method for detecting the Q2 level is a biological sample and comparing that level to a normal Q2 level can be used to detect, screen, diagnose, or otherwise determine a person's susceptibility to Alzheimer's disease such as, for example, the presence or absence of Alzheimer's disease, of symptoms of this disease, of factors leading to or associated with this disease, of likelihood of developing this disease, and the like. In one embodiment, a decline in Q2 level correlates to an increased likelihood for developing Alzheimer's disease. In another embodiment, a decline in Q2 level correlates to an increase in β-amyloid aggregation. The method may further include screening for an apolipoprotein E genotype, which is associated with Alzheimer's disease.

2 Claims, 16 Drawing Sheets

FIG. 1: ANIMAL WEIGHTS AS A FUNCTION OF AGE

FIG. 2: LIVER WEIGHTS AS A FUNCTION OF AGE

FIG. 3: MICROSOMAL PROTEIN PER GRAM LIVER AS A FUNCTION OF AGE

FIG. 4: LIFE TABLE ANALYSIS OF ANIMAL SURVIVAL

FIG. 5: MORTALITY RATE VERSUS AGE

FIG. 6: EFFECT OF AGE ON THE HEPATIC, MICROSOMAL Q5 LEVELS

FIG. 7: THE EFFECT OF AGE ON THE STRESS RESPONSIVE LEVELS OF Q5

FIG. 8: EFFECT OF AGE ON THE HEPATIC, MICROSOMAL Q2 LEVELS

FIG. 9: THE EFFECT OF AGE ON THE STRESS RESPONSIVE LEVELS OF Q2.

FIG. 10: EFFECT OF AGE ON THE HEPATIC, MICROSOMAL ERp72 LEVELS

FIG. 11: EFFECT OF AGE ON THE HEPATIC, MICROSOMAL BIP LEVELS

FIG. 12: EFFECT OF AGE ON THE HEPATIC, MICROSOMAL CALNEXIN LEVELS

FIG. 13: EFFECT OF AGE ON THE HEPATIC, MICROSOMAL CALRETICULIN LEVELS

A
B
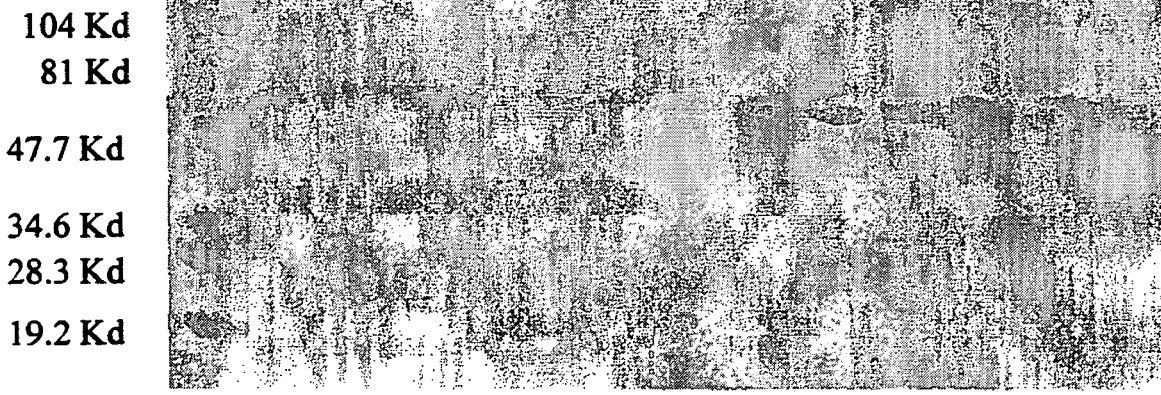
FIGURE 14
Immunoblots with A) Chicken Polyclonal antibodies to Q2 and B) Monoclonal Antibodies to B-amyloid 1-42. Channel 1-Prestrained Standards; Channels 2-Rat, Hepatic Microsomes; Channels 3-7 & 9-14--15μl of CSF from Normal,Human Subjects,Ages 6 Months to 59 Years; Channel 8 - Purified Q2

Immunoblots with A) Polyclonal antibodies to q2 and B) to B-amyloid 1-42. Channel 1 Prestained Srandards; Channels 2-CSF; Channel 3-Seperated by afinity chromatography with anti-B-amyloid antibodies; Channel 4-CSF Seperated by affinity chromatography with anti-Q2 antibodies

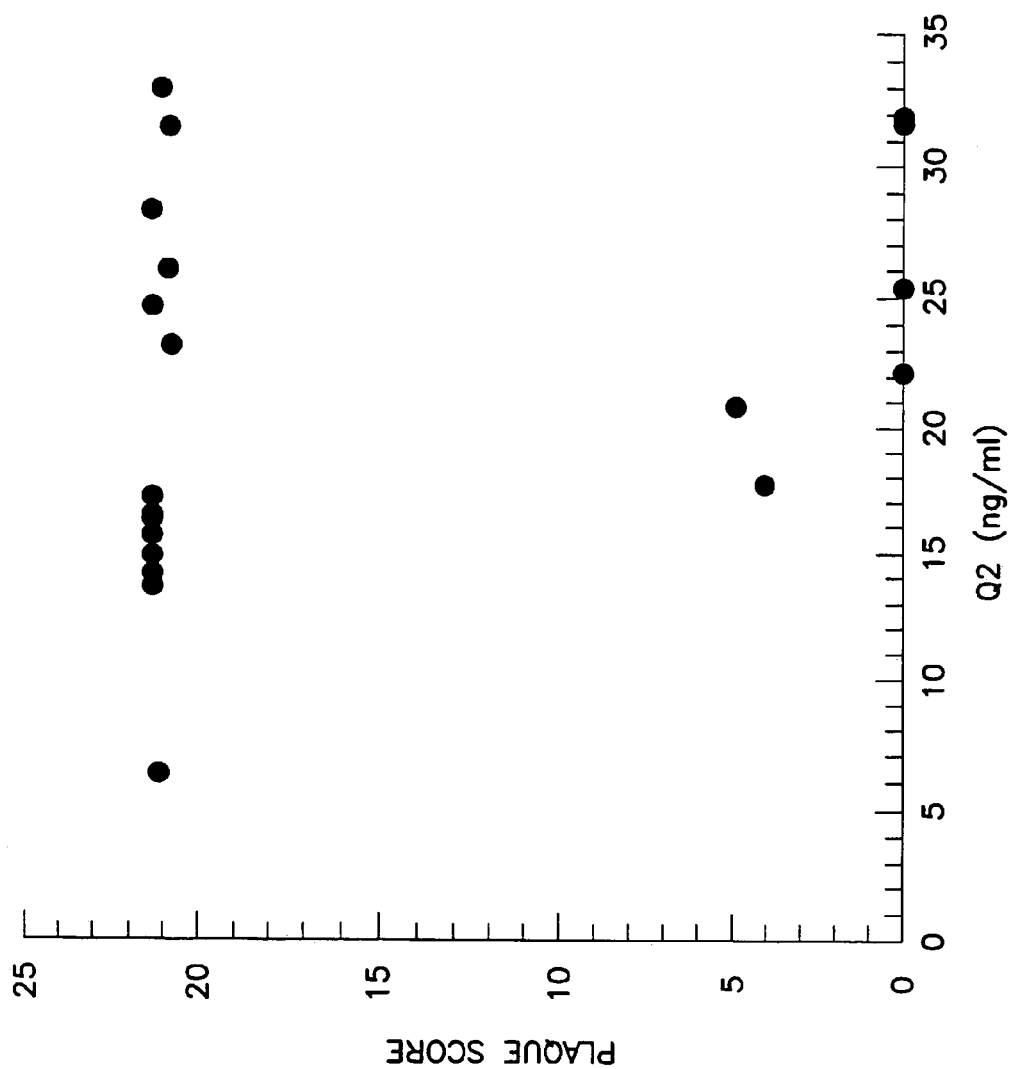
FIG. 16: THE CSF CONCENTRATIONS OF Q2 COMPARED TO SENILE PLAQUE SCORES IN THE BRAINS OF PARTICIPANTS IN THE NUN STUDY.

COMPLEX OF A CHAPERONE PROTEIN WITH AMYLOID

This application is a national stage filing under 35 U.S.C. § 371 of PCT/US99/25593 (filed Oct. 29, 1999), which in turn claims priority to application 60/123,564 (filed Mar. 10, 1999) and application 60/106,398 (filed Oct. 30, 1998).

BACKGROUND OF THE INVENTION

Numerous physiological problems, such as a loss in muscle mass, a failure of the immune system, decreases in the maximal synthesis and release of hormones (e.g. insulin or growth hormone), loss of renal function, and decreases in cognitive skills occur with aging. These problems lead to an overall decline in functional capacity. Several models have been advanced to explain these age-related physiological problems. Such models include, for example, increased programmed cell death, i.e. apoptosis; accumulation of oxidant damage; failure of the cell to maintain the telomeres at the ends of the chromosomes; and defects in responding to stress. The observed age-related defects in responding to stress may involve chaperone proteins.

At the cellular level the most important stress proteins are the chaperones. Chaperones play an important role in cellular function. They help to realign proteins into their native state, thereby renaturing damaged proteins and aid the final steps of protein folding by directing newly synthesized proteins into their final, optimal structure. Chaperones also help stabilize the final protein product, such as by the formation of intra- and intermolecular disulfide bonds. One such family of chaperones is known as thiol:protein disulfide oxidoreductases (TPDOs). Studies of the stress proteins and chaperones support the concept that many of the age-related functional declines are associated with decreases in the activity of the chaperone systems. Decreased levels and activity of chaperones can result in increased formation of improperly folded and insoluble masses of proteins.

Insoluble masses, or plaques, of the β-amyloid protein, a 38 to 43 amino acid peptide derived from the amyloid precursor protein, form in the brain of older persons suffering from Alzheimer's disease. Amyloid precursor protein is an intrinsic membrane protein that is synthesized in the endoplasmic reticulum. During synthesis and insertion into the plasma membrane, β-amyloid is cleaved off the amyloid precursor protein and secreted into the intercellular space.

In physiological solutions β-amyloid readily aggregates to form plaques characteristic of Alzheimer's disease. However, Alzheimer's disease is complex and involves more than mere overexpression of the β-amyloid peptide. The neuropathology of Alzheimer's disease is characterized by extensive neuronal cell loss and deposition of numerous senile plaques and neurofibrillary tangles in the cerebral cortex. Although small numbers of classic senile plaques develop in the normal brain with age, large numbers of the plaques are found almost exclusively in Alzheimer's patients.

One study showed that when cerebrospinal fluid is added to β-amyloid, β-amyloid does not aggregate, suggesting that cerebrospinal fluid includes a component that inhibits β-amyloid aggregation. This indicates that cerebrospinal fluid of subjects that are free of Alzheimer's disease may include a component that prevents formation of senile plaques. This component could be a chaperone. Thus, it is desirable to better characterize the role of chaperones in processing of amyloid precursor protein, forming β-amyloid plaques, and Alzheimer's disease. Proper folding or processing of the amyloid precursor protein or β-amyloid may be involved in the etiology of Alzheimer's disease.

Alternatively, a patient with Alzheimer's disease may have a protein that enhances nucleation of β-amyloid plaques. One theory suggests that apolipoprotein E may play a role in Alzheimer's disease. Apolipoprotein E exists in at least 3 allelic forms known as $apoE_2$, $apoE_3$, and $apoE_4$. Evidence indicates that a person who has at least one allele of apolipoprotein $E_4$ ($apoE_4$) is more susceptible to Alzheimer's disease, suggesting that the protein product of $apoE_4$ may play a role in Alzheimer's disease. Moir et al., Biochemistry, 38: 4595–4603 (1999). For example, $apoE_4$ may contribute to the nucleation or formation of β-amyloid plaques by contributing to the aggregation of β-amyloid.

Previously, Alzheimer's disease studies have focused on overproduction of β-amyloid. For instance, many laboratories have investigated the role of proteases involved in cleaving the precursor protein to produce β-amyloid. Yet a number of studies have shown that, with the exception of some rare genetic forms of early onset Alzheimer's disease and the early Alzheimer's disease seen with Down's syndrome, patients with Alzheimer's disease actually have lower concentrations of β-amyloid in their cerebrospinal fluid than age-matched controls. Further, a recent study of transgenic mice having an amyloid precursor protein gene lacking the Kunitz-protease inhibitor domain showed that the increased concentration of β-amyloid cannot be explained by a rise in expression of amyloid precursor protein, which appeared to remain unchanged with age. These studies indicate that β-amyloid levels alone are not enough to explain Alzheimer's disease. Thus, it is desirable to better characterize the role of chaperones and processing of amyloid precursor protein in forming β-amyloid plaques and in Alzheimer's disease. Proper folding or processing of the amyloid precursor protein or β-amyloid may be involved in the etiology of Alzheimer's disease.

Furthermore, at present the only method to detect a propensity for formation of β-amyloid plaque or Alzheimer's disease or the presence of such plaques or disease includes dissection of the brain or culturing of brain cells of the subject. Such invasive procedures are, of course, undesirable for most subjects. This is particularly so, since as outlined above, even after such dissection, it previously would have been unclear how to test for certain factors leading to plaque formation or disease. This demonstrates a need for a method to detect the propensity for or presence of plaques or disease in a living, intact subject.

SUMMARY OF THE INVENTION

The present invention generally relates to a composition and method of detecting this composition that meet the needs described above. The present invention includes an isolated complex of a chaperone and β-amyloid protein. Preferably the complex includes the chaperone Q2 and β-amyloid. The complex can be natural or produced by biotechnological methods and can be purified.

The present invention also includes a method for detecting Q2 levels. The method can include an immunoassay, a method of chemical detection, a method of physical detection, or the like. Preferably the method employs an immunoassay. The method for detecting the Q2 levels can be employed as a reagent in a clinical or scientific laboratory, as a method for determining the propensity of a biological system to form plaques of β-amyloid or for determining the presence or likelihood of Alzheimer's disease or symptoms associated with Alzheimer's disease.

BRIEF DESCRIPTION OF THE DRAWINGS

FIG. 14A illustrates an immunoblot of biological samples with polyclonal antibodies to Q2.

FIG. 14B illustrates an immunoblot of biological samples with monoclonal antibodies to $\beta$-amyloid 1–42.

FIG. 16 illustrates cerebrospinal fluid concentrations of Q2 compared to senile plaque scores measured from participants in the nun study described in Example 5.

DETAILED DESCRIPTION OF THE INVENTION

Figure 1:
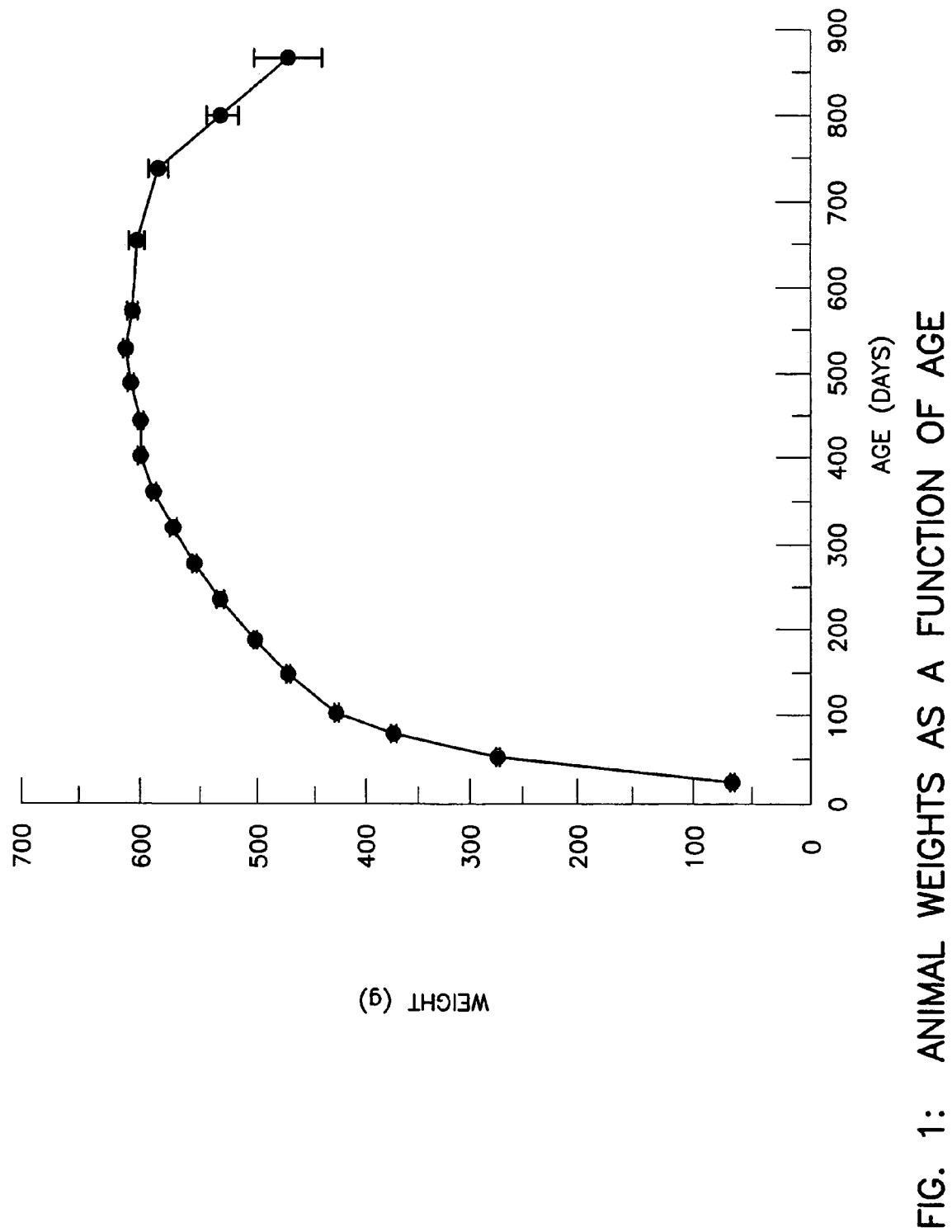
FIG. 1 illustrates rat weights as a function of age.

The present invention relates to a complex of a chaperone protein with $\beta$-amyloid, methods for detecting levels of Q2, methods for employing such detection in diagnosis of Alzheimer's disease, and methods of enhancing levels of this chaperone protein to treat or prevent Alzheimer's disease. In particular, the present invention is directed to an isolated complex of $\beta$-amyloid and the chaperone Q2, methods to detect levels of Q2 in, for example, clinical or autopsy samples, methods to diagnose Alzheimer's disease based on detecting a decrease in concentration of Q2 in clinical samples, such as cerebrospinal fluid, and methods of treating Alzheimer's disease by stimulating Q2 production or by administering Q2.

Alzheimer's Disease and $\beta$-Amyloid

Alzheimer's disease includes formation of $\beta$-amyloid plaques in the brains of subjects with the disease. The plaques form from aggregates of $\beta$-amyloid, which form from cleavage of the amyloid precursor protein and secretion into the intercellular space. $\beta$-Amyloid freely aggregates in solution in laboratory systems and forms aggregates similar to the plaques formed in Alzheimer's disease.

Amyloid precursor protein, $\beta$-amyloid, and various fragments of $\beta$-amyloid have been characterized. Known features of amyloid precursor protein and $\beta$-amyloid include mammalian genes encoding them, recombinant expression systems (e.g. vectors, plasmids, and the like) for these proteins, methods of producing these proteins, protein sequences and structures, and proteases that cleave the amyloid precursor to $\beta$-amyloid. Neither amyloid precursor protein, $\beta$-amyloid, nor any of the various fragments of $\beta$-amyloid have previously been observed to interact with a chaperone protein.

$\beta$-Amyloid can be made and/or isolated in a variety of forms. The most prevalent form of $\beta$-amyloid in mammalian tissues is $\beta$-amyloid 1–42, where the numbering represents the number of amino acids starting at the amino terminus of complete $\beta$-amyloid, which has from 38–43 amino acids depending on species. The second most prevalent form of $\beta$-amyloid in mammalian tissues is $\beta$-amyloid 1–38.

$\beta$-Amyloids have been produced by chemical and/or biotechnical methods, characterized, and shown to have many of the properties of complete $\beta$-amyloid. $\beta$-Amyloid as used herein refers to all of the various forms of $\beta$-amyloid, including glycosylated, nonglycosylated, forms of various lengths, and the like.

Chaperones

Chaperones (also known as chaperone proteins, and including chaperonins and certain heat shock proteins) catalyze folding, formation of tertiary structure, formation of quaternary structure, and/or other processing to make an active protein. As described herein, several chaperones can decline in level with age and can be correlated with age-related diseases and disorders. In particular, tissue levels of one or more of the chaperones BiP, calreticulin, calnexin, Erp72, Q2, and Q5 can decrease with age of a mammal, such as a rodent or a human, and can correlate with a disease. Chaperones include a family known as a thiol:protein disulfide oxidoreductase (TPDO). A TPDO represents a preferred chaperone of the present invention. A preferred TPDO is TPDO-Q2. TPDO-Q2 has also been called ERp57 and GRp58. As used herein, Q2 refers to any of the common names for this protein, including TPDO-Q2, ERp57, and GRp58 and all naturally occurring variant forms of this protein, including glycosylated and nonglycosylated forms.

Chaperones are, in general, well studied and/or characterized proteins. Well characterized features of numerous chaperones include the genes encoding them in organisms ranging from bacteria to humans, recombinant expression systems' (e.g. vectors, plasmids, and the like) for these proteins, methods of producing these proteins, protein sequences and structures, certain protein substrates, and certain biological functions. Chaperones have not previously been observed to decrease with age of a mammal nor have they been implicated in Alzheimer's disease or formation of $\beta$-amyloid plaques.

A decline in chaperone synthesis can result from a decline in chaperone transcription. To determine whether the amount of chaperones declines with age in, tissues and/or fluids relevant to Alzheimer's disease and/or $\beta$-amyloid plaque formation, the concentration of specific mRNAs for various chaperones can be studied by known methods, for example, standard hybridization techniques.

A Complex of Chaperone Q2 and $\beta$-Amyloid

Although other chaperones may be present in cerebrospinal fluid, only Q2 has been identified in cerebrospinal fluid. Q2 levels can decrease relative to normal Q2 levels in mammalian tissue with age. "The term normal Q2 levels" as used herein includes the mean concentration of Q2 that can typically be found in cerebrospinal fluid from a control population. Suitable control populations include, for example, young people, elderly people without Alzheimer's disease, and the like. A normal Q2 level can be about 27±2 ng/ml.

Q2 can form a complex with β-amyloid. This complex can be isolated from cerebrospinal fluid and created in the laboratory. Q2 and β-amyloid are believed to form a strongly bound complex. For instance, immunoblots evidence very little dissociation of the complex. The complex of Q2 and β-amyloid is believed to be an intermediate in normal processing of amyloid precursor in subjects not suffering from Alzheimer's disease. A decrease in the level of Q2 relative to normal Q2 levels in an aging animal can lead to decreased amounts of the complex and increased amounts of free β-amyloid. Increased amounts of β-amyloid can give rise to increased depositions of amyloid plaques associated with Alzheimer's disease.

The complex of Q2 and β-amyloid can be isolated from cerebrospinal fluid, purified, and characterized by common methods of protein chemistry. For example, the complex can be isolated and/or purified by affinity chromatography with a system having affinity for one or either of Q2 or β-amyloid. The complex can then be further purified by other forms of chromatography, such as separation on a Sephacryl column and/or a monoQ column. Following isolation and/or purification, the complex can be characterized by employing standard methods such as peptide mapping, sequencing, the PAS reaction (periodic acid-Schiff reaction), and matrix assisted laser desorption ionization-time of flight mass spectrometry (MALDI-TOF).

The complex of Q2 and β-amyloid can be glycosylated in natural systems. Under most circumstances outside the complex, neither Q2 nor β-amyloid appear to be glycosylated. Typically the complex is glycosylated, for example, N-glycosylated on asparagine residues with complex oligosaccharides.

Detecting Q2 Levels

The complex of Q2 and β-amyloid and the unbound components Q2 and β-amyloid can be detected by methods known for detecting proteins, sugars, and/or glycosylated proteins. The complex has a molecular weight of about 62 kD on gently or moderately denaturing gel electrophoresis and is recognized by antibodies to either Q2 or β-amyloid. Polyclonal or monoclonal antibodies recognizing either Q2 or β-amyloid are known in the art and can be produced by standard methods. Such antibodies can be labeled or otherwise employed in standard immunoassays. Preferred standard immunoassays include ELISA assays, immunoblots, sandwich assays, enhanced chemiluminescence, and the like. Additional methods for detecting the complex or its unbound components include fluorescence polarization assay, standard protein purification by column and affinity chromatography, proteolytic cleavage followed by Edman degradation analysis, MALDI-TOF, and time-of-flight mass spectrometry.

Methods for detecting Q2 levels in biological samples can be employed in a method for detecting, determining, examining, diagnosing, screening for, or otherwise assessing a patient's or subject's susceptibility to Alzheimer's disease. The term "susceptibility to Alzheimer's disease" as used herein includes the presence or absence of Alzheimer's disease, of symptoms of this disease, of factors leading to or associated with this disease, of likelihood of developing this disease in a subject or patient, and the like. As used herein, factors leading to or associated with this disease include formation of β-amyloid plagues, disorders in processing of amyloid precursor protein, and the like.

As used herein biological samples include biological material such as a tissue, cell, or fluid sample from an animal or human in need of being screened for or suspected of being susceptible to or suffering from deposition of β-amyloid plaques, disorders in processing of amyloid precursor protein, Alzheimer's disease, likelihood of developing Alzheimer's disease, and the like. Biological samples can also include laboratory samples from an experimental animal, cell, or culture being examined for their propensity to form β-amyloid plaques or aggregates or to improperly process amyloid precursor protein. The biological sample including, for example, tissues or cells, such as liver, platelets, serum, or skin, can be recovered from a living animal or patient by methods such as needle biopsy, venapuncture, or skin scraping. In one aspect of the invention, the biological sample includes biological material from the central nervous system of a human or an animal. A preferred biological sample includes biological material from cerebrospinal fluid for assessing the susceptibility to Alzheimer's disease in living animals or patients. Cerebrospinal fluid can be recovered by spinal tap, during surgical procedures, or by any of the variety of methods known to those of skill in the art.

Generally the decline in Q2 levels relative to normal Q2 correlates to the susceptibility to Alzheimer's disease. The level of Q2 or Q2 level includes the level of free Q2 in the biological sample, the level of Q2 bound in complex with β-amyloid, the levels of free Q2 plus bound Q2, and preferably total Q2. A decline in the Q2 level correlates to an increased susceptibility to Alzheimer's disease. An increased susceptibility, as used herein, refers to it being more probable than not that Alzheimer's disease, at least one symptom of the disease, at least one factor leading to or associated with this disease, likelihood of developing this disease, or the like is present in a patient or subject. For example, in one embodiment a decline in Q2 level of at least 35% relative to a normal Q2 level correlates with a 100% likelihood of developing Alzheimer's disease. In another embodiment, the aggregation of β-amyloid in an animal or human can be detected by determining the level of Q2 in the biological sample. A decline in Q2 levels relative to normal Q2 levels correlates to and indicates an increased susceptibility to an increase in β-amyloid aggregation. By detecting the aggregation of β-amyloid, the formation of β-amyloid plaques is also detected.

The susceptibility to Alzheimer's disease may also be determined by correlating the level of free Q2, the level of β-amyloid, and the level of Q2: β-amyloid in complex. A relevant decline in Q2 levels relative to normal Q2 levels includes a decline of about 35%, preferably about 50%, more preferably about 65%. Such a relevant decline correlates to an increased susceptibility to Alzheimer's disease, for example, to factors leading to or associated with Alzheimer's disease, particularly β-amyloid plaque formation; to Alzheimer's disease; to symptoms associated with Alzheimer's disease; to developing Alzheimer's disease; or the like.

The decline in Q2 levels relative to normal Q2 levels can be correlated with symptoms characteristic of Alzheimer's disease by comparing Q2 levels with neuropsychiatric function measurements. Neuropsychiatric function measurements can be made by conducting, for example, a neuropsychiatric evaluation, a complete history, and a physical examination and evaluating this information based on criteria defined by, for example, DSMIII-R and NinCDS-ADRDA.

In some instances, individuals who have Q2 levels of about normal can also be susceptible to Alzheimer's disease.

For example, individuals having normal Q2 levels but an apoE$_4$ allele have an increased susceptibility to Alzheimer's disease. There may be other risk factors for Alzheimer's disease that result in an increased susceptibility to Alzheimer's disease in the presence of normal Q2 levels.

Enhancing Q2 Levels

Q2 levels can be enhanced by administering a drug suitable for increasing Q2 expression or by administering Q2. Administering Q2 includes administering Q2 in a form or precursor of this protein, in a manner that increases Q2 levels in, for example, the cerebrospinal fluid. Enhancing Q2 levels can increase the amount of complex of Q2 with β-amyloid, increase the level of appropriately processed β-amyloid and/or amyloid precursor protein, and/or decrease the amount of β-amyloid plaque in a subject, and the like.

Q2 can be administered in a pharmaceutically acceptable vehicle to the cerebrospinal fluid by methods such as injection, by an intracerebroventricular pump, and the like. Alternatively, Q2 can be administered as a precursor gene or vector encoding Q2, which can be targeted for the central nervous system and provide expression and increased levels of Q2. Vectors that can encode Q2 and that will express protein in and/or target brain cells are known to those of skill in the art.

Preferably Q2 or a drug suitable for enhancing Q2 expression is administered in an amount effective to increase Q2 level in, for example, cerebrospinal fluid, to increase the amount of complex of Q2 with β-amyloid, to increase the level of appropriately processed β-amyloid and/or amyloid precursor protein, and/or to decrease the amount of β-amyloid plaque in a subject, or the like. Further, such administration can affect the course or outcome of Alzheimer's disease. An "effective amount" of Q2 or a drug suitable for enhancing Q2 expression is an amount sufficient to prevent, treat, reduce, and/or ameliorate the symptoms and/or underlying causes of Alzheimer's disease including the level of Q2, the level of appropriately processed β-amyloid and/or amyloid precursor protein, and/or the amount of β-amyloid plaque in a subject, or the like. In some instances, an "effective amount" is sufficient to eliminate the symptoms of the disease and, perhaps, overcome the disease itself. In the context of the present invention, the terms "treat" and "therapy" and the like refer to alleviate, slow the progression, prophylaxis, attenuation, or cure of existing disease. "Prevent" as used herein, refers to putting off, delaying, slowing, inhibiting, or otherwise stopping, reducing, or ameliorating the onset of such brain diseases or disorders.

The present invention may be better understood with reference to the following examples. These examples are intended to be representative of specific embodiments of the invention, and are not intended as limiting the scope of the invention.

EXAMPLES

Example 1

Characterization of the Effect of Aging on Chaperone Concentration in Animal Hepatic Microsomes The effect of aging on chaperone concentration was determined to demonstrate a decrease in concentration that can be linked to age-related disorders such as plaque deposition or Alzheimer's disease.

Materials and Methods

The animals used in this study were male, specific pathogen free, Sprague-Dawley rats purchased at age 21 days from Harlan Laboratories (Madison, Wis.). For the remainder of their lives, they were housed in a windowless, controlled environment, "state-of-the-art," barrier facility with a constant temperature of 22° C.±2° and a 12 hour on and 12 hour off light cycle. The humidity was maintained at 50%±20%. Two animals were housed in, each cage and the animals had free access to food and water. Each cage containing test animals was equipped with an air filter cover. Ten percent of the cages did not have filters. The animals in the cages without filters were maintained as "sentinels" to determine whether there was any break in the sterile conditions. These animals were routinely replaced with new batches of young animals. They did not show an increase in mortality, indicating the colony was pathogen free.

All animals were removed from their cage once a week when the cages were cleaned and every four to six weeks when the animals were weighed. These procedures were performed under clean conditions. Any person who entered the animal room wore sterile gloves, gowns, and masks. The animals were fed a diet based on the AIN76A recommendations with the exception that the carbohydrate was supplied as 40% starch and 25% sucrose (BioServe, Frenchtown, N.J.). The carbohydrate composition was changed to accommodate a preference for the diet to consist of pellets instead of a powder and to reduce the incidence of the obesity which is associated with high sucrose diets. Potassium citrate (6.5%) was added to prevent vascular disease. The dietary conditions met NRC nutritional standards for the adult rat. (NRC 1978).

Figure 2:
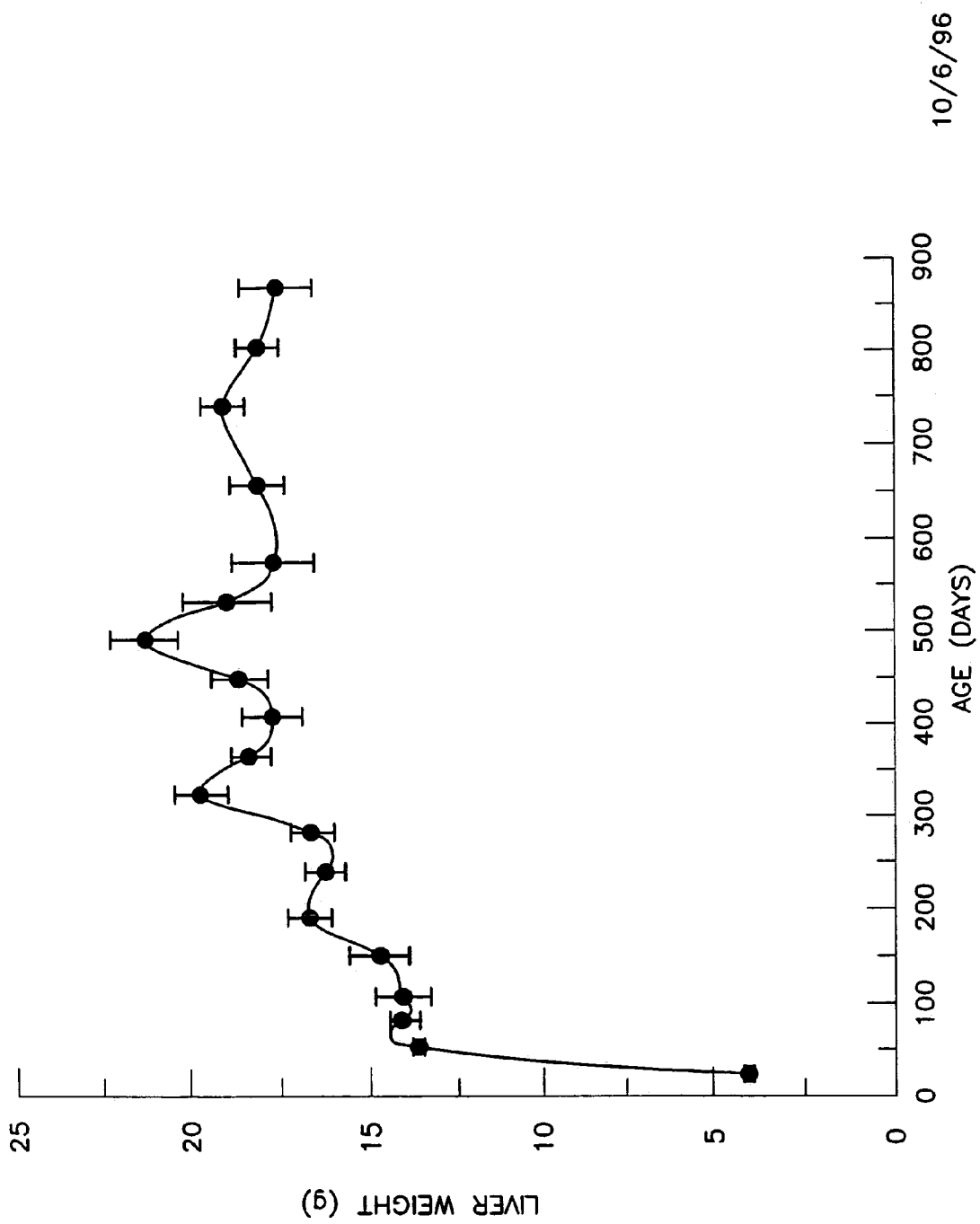
FIG. 2 illustrates rat liver weights as a function of age.
Figure 3:
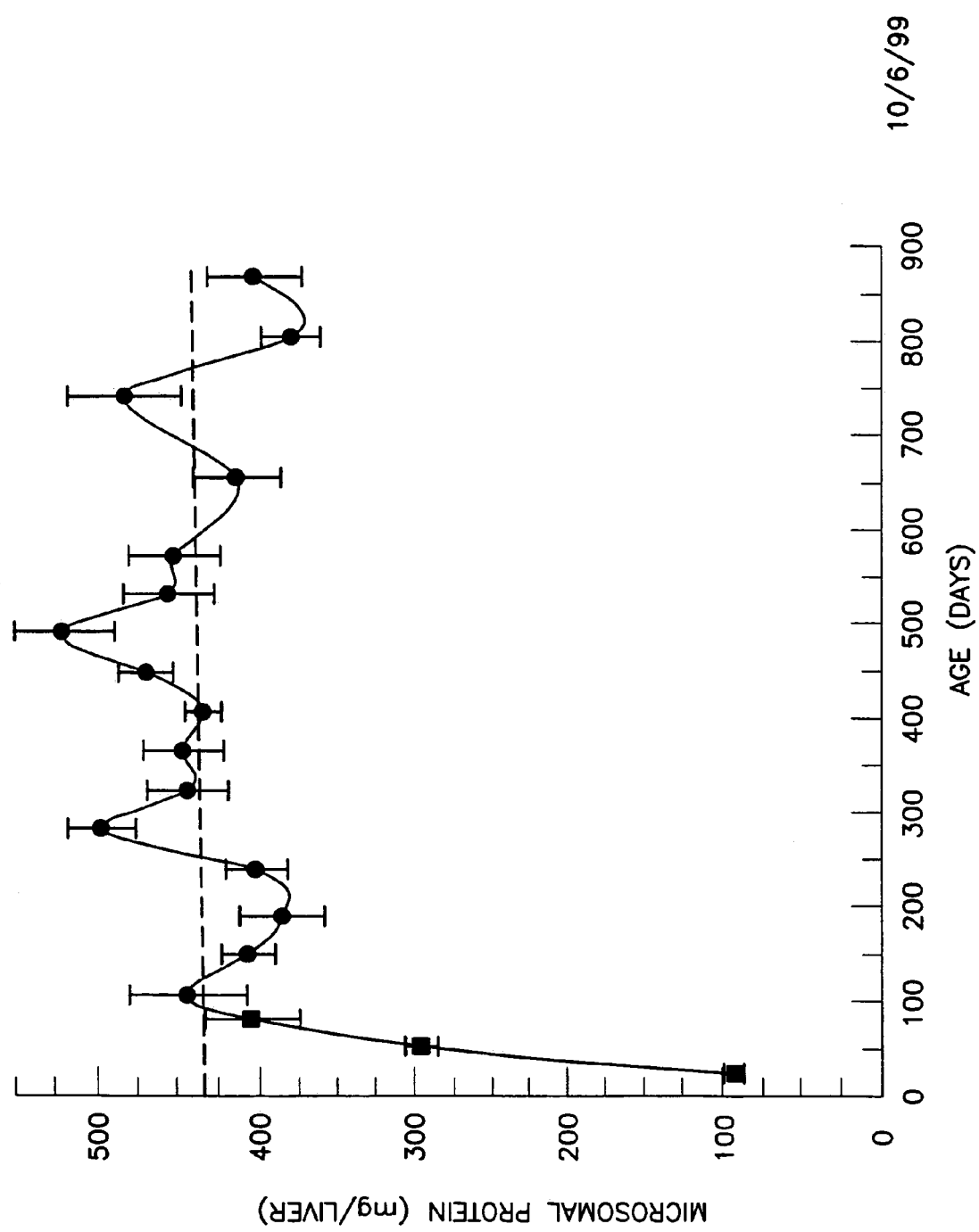
FIG. 3 illustrates the amount of microsomal protein per gram of liver as a function of age.
Figure 4:
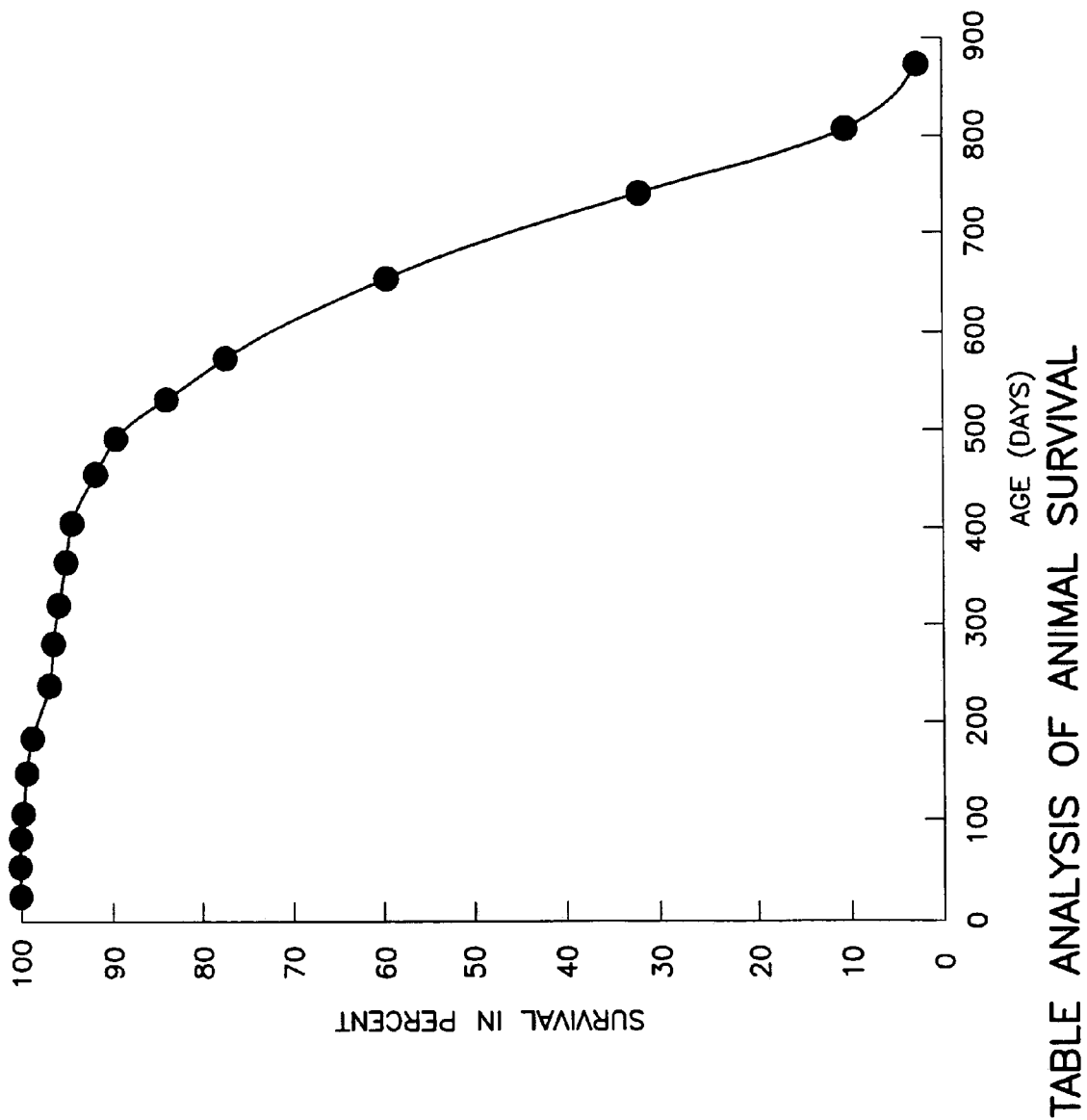
FIG. 4 illustrates a survival rate of rats as a function of age.
Figure 5:
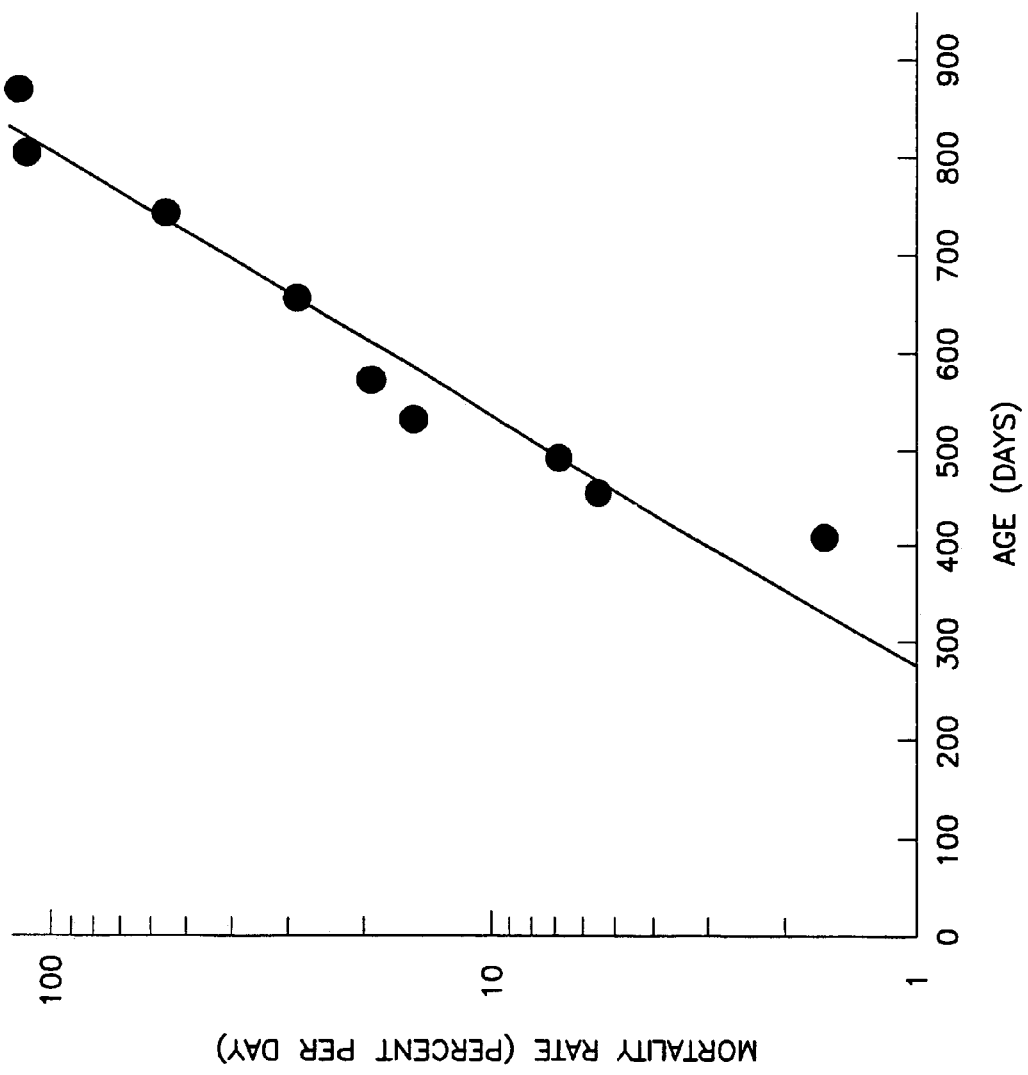
FIG. 5 illustrates a mortality rate of rats as a function of age.

The animals reached and maintained an adult weight of about 600 g (FIG. 1). However, after the age of 750 days, their average weights declined to 475 g. This decline in the average weight of the animals that survived to the end of the study was the same as the average weight of the total population. The average adult liver weight was 17.5 g and remained there for their entire adult lives (FIG. 2). The milligram of microsomal protein per gram of liver showed no significant change with age (FIG. 3). There was no significant mortality until the age of about 500 days (FIG. 4). After 500 days, the mortality rate showed a Gompertz effect with a doubling every 96.1 days (FIG. 5). Humans show a similar doubling in mortality every decade.

For the first 18 months, six animals were killed at six week intervals. For the remaining 12 months, the animals were killed at three month intervals. Tissue samples were obtained from approximately one-third of the animals. The remainder died from natural causes.

Microsomes were prepared by differential centrifugation according to Srivastava et al., *J. Biol. Chem.*, 265:8392–99 (1990). Microsomal suspensions were frozen and maintained at −70° C. for the determination of the concentration of chaperones. The following chaperones were examined: BiP, calreticulin, calnexin, ERp72, Q2, and Q5. Chaperones were prepared by methods known in the art. The microsomal content of chaperones was determined by immunoblotting according to Zhou et al., *Arch. Biochem. Biophys.*, 322: 390–94 (1995); Zhou et al. (1996); and Chen et al., *Biochemistry*, 25: 8299–8306 (1996). A pooled microsomal suspension was run on each gel and used as a standard. The chaperone content of the microsomes was calibrated against purified chaperones. The immunoassays were run in the linear range for the individual chaperones.

Chaperones were prepared by methods known in the art. Srivastava et al., *J. Biol. Chem.*, 265: 8392–99 (1991); Chen et al., *Biochemistry*, 25: 8299–8306 (1996).

Immunoblotting was done according to the method of Towbin et al., *Proc. Natl. Acad. Sci. USA*, 76: 4350–4354 (1979). See also Srivastava et al., *J. Biol. Chem.*, 265: 8392–8399 (1991); Zhou et al., *Arch. Biochem. Biophys.*, 322: 390–394 (1995); Zhou et al., *Chem. Res. Toxicol.*, 9: 1176–1182 (1996); and Chen et al., *Biochemistry*, 25: 8299–8306 (1996). The proteins were first separated by SDS-PAGE. Laemmli, *Nature*, 227: 680–685 (1970). The proteins then were transferred to PVDF membranes (Immobilon P, Millipore Corp), and the membranes were reacted with chicken anti-chaperon antibodies. This was followed by goat anti-chicken IgY antibody coupled to alkaline phosphatase. The indicator dye used is a combination of nitroblue tetrazolium and 5-bromo-4-chloro-3-indolyl phosphate (BioRad, Richmond Calif.). The density of the bands was determined on a flat bed scanner (UMAX, Taiwan, R.O.C.) and analyzed using NIH Image (version 1.61) on a Power PC (Apple Computer). The concentration was determined by comparison to various concentrations corresponding to the average density of three channels on each gel containing a suspension of reference microsomes. The microsomal standards were calibrated against several concentrations of the purified proteins. The determinations of the chaperones in the microsomes were all within the linear range of the immunoassays.

Polyclonal antibodies to all chaperones, except for BiP, were developed in laying hens as described by Damiani et al., *J. Biol. Chem.*, 263:340–343 (1988) and Chen et al., *Biochemistry*, 25: 8299–8306 (1996). The specificity of these antibodies has been verified in previous studies. Srivastava et al., *J. Biol. Chem.*, 265: 8392–8399 (1991); Zhou et al., *Arch. Biochem. Biophys.*, 322: 390–394 (1995); Zhou et al., *Chem. Res. Toxicol.*, 9: 1176–1182 (1996); Chen et al., *Biochemistry*, 25, 8299–8306 (1996). Antibodies to BiP were obtained from StressGen (Vancouver, BC, Canada). Additionally, the antibodies prepared to calreticulin also were used to probe for calnexin because the lumenal portion of calnexin is highly homologous to calreticulin. Zhou et al. (1996); Chen et al. (1996); Cala et al. (1993).

Results

Figure 6:
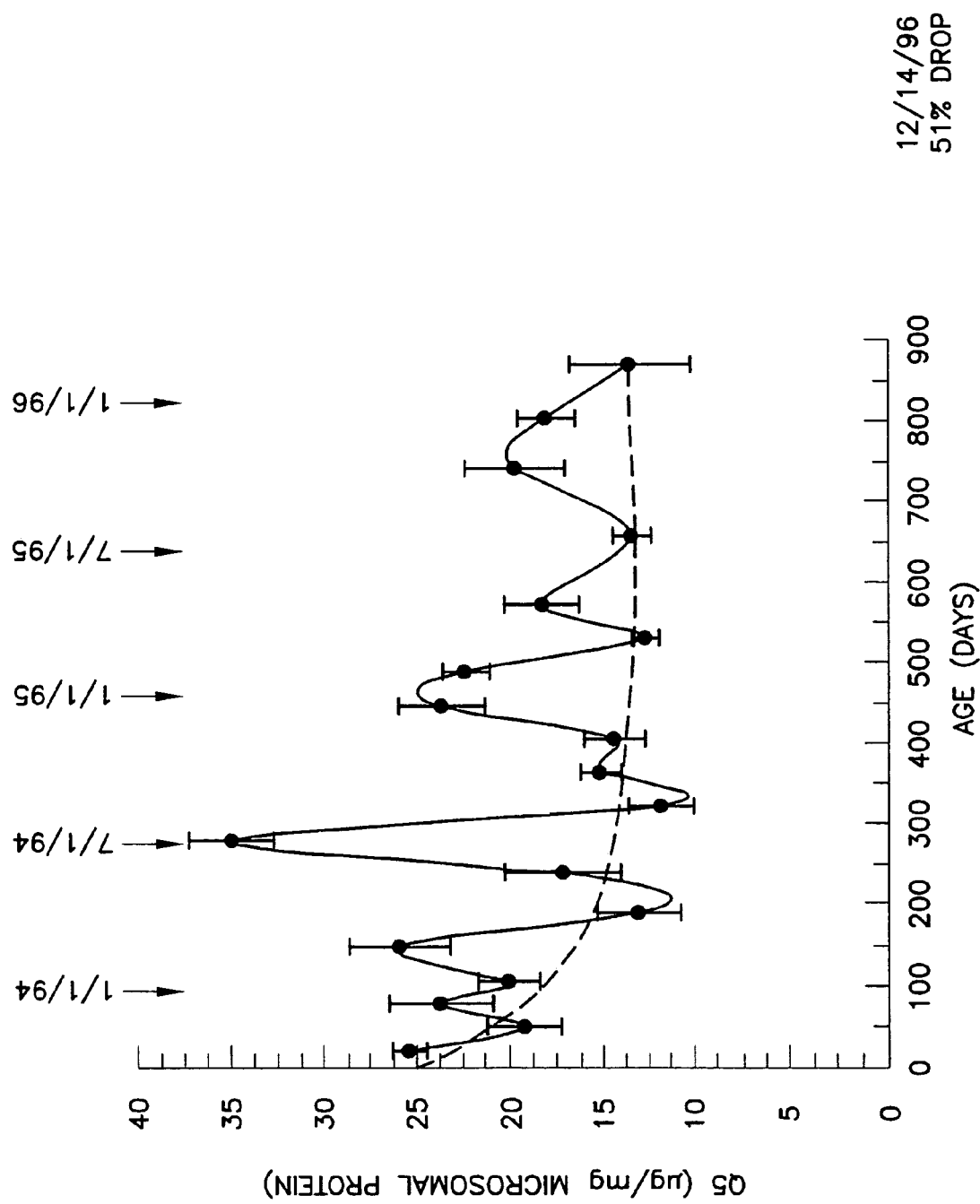
FIG. 6 illustrates rat hepatic, microsomal Q5 levels as a function of age.
Figure 7:
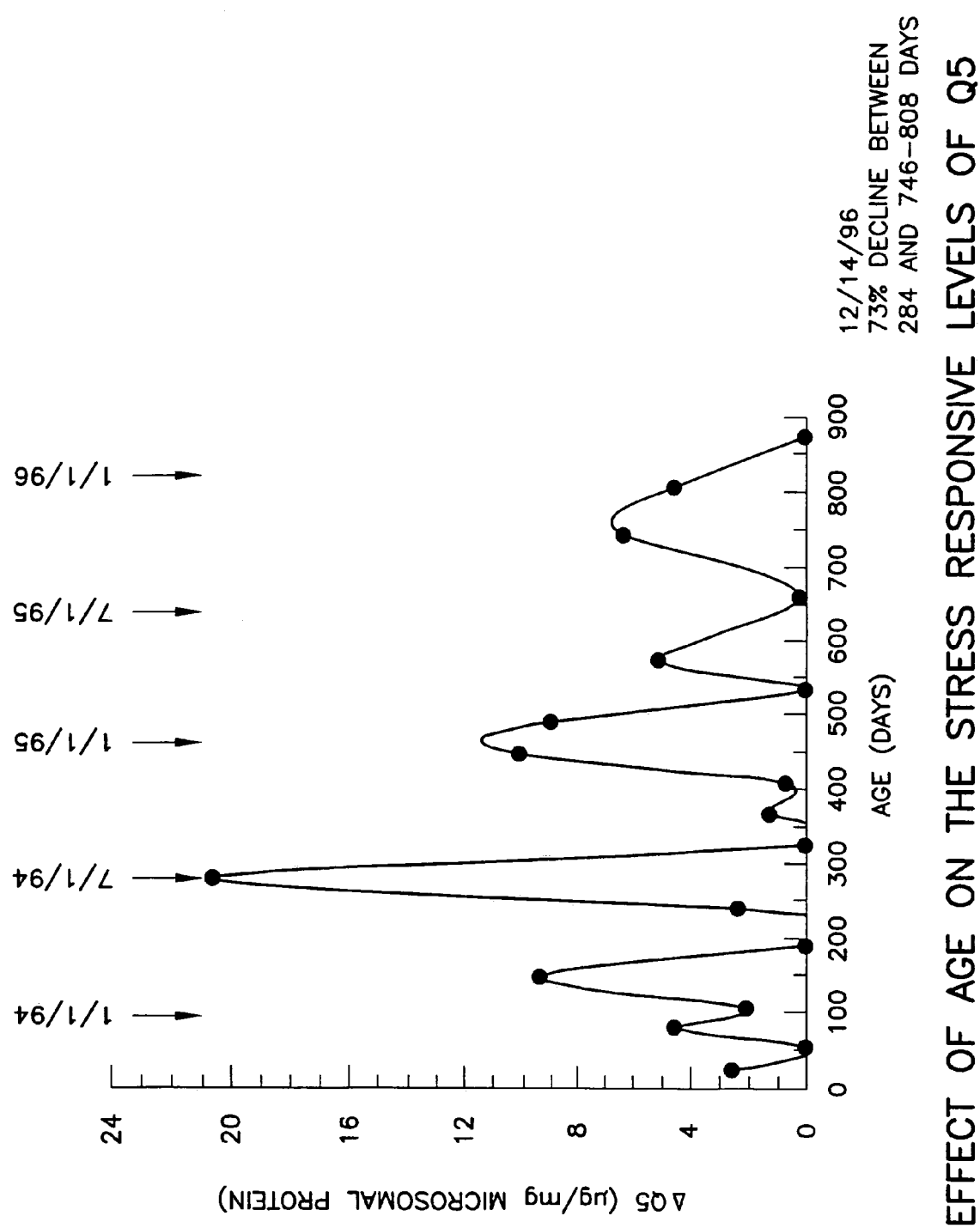
FIG. 7 illustrates rat stress-responsive levels of Q5 as a function of age.
Figure 8:
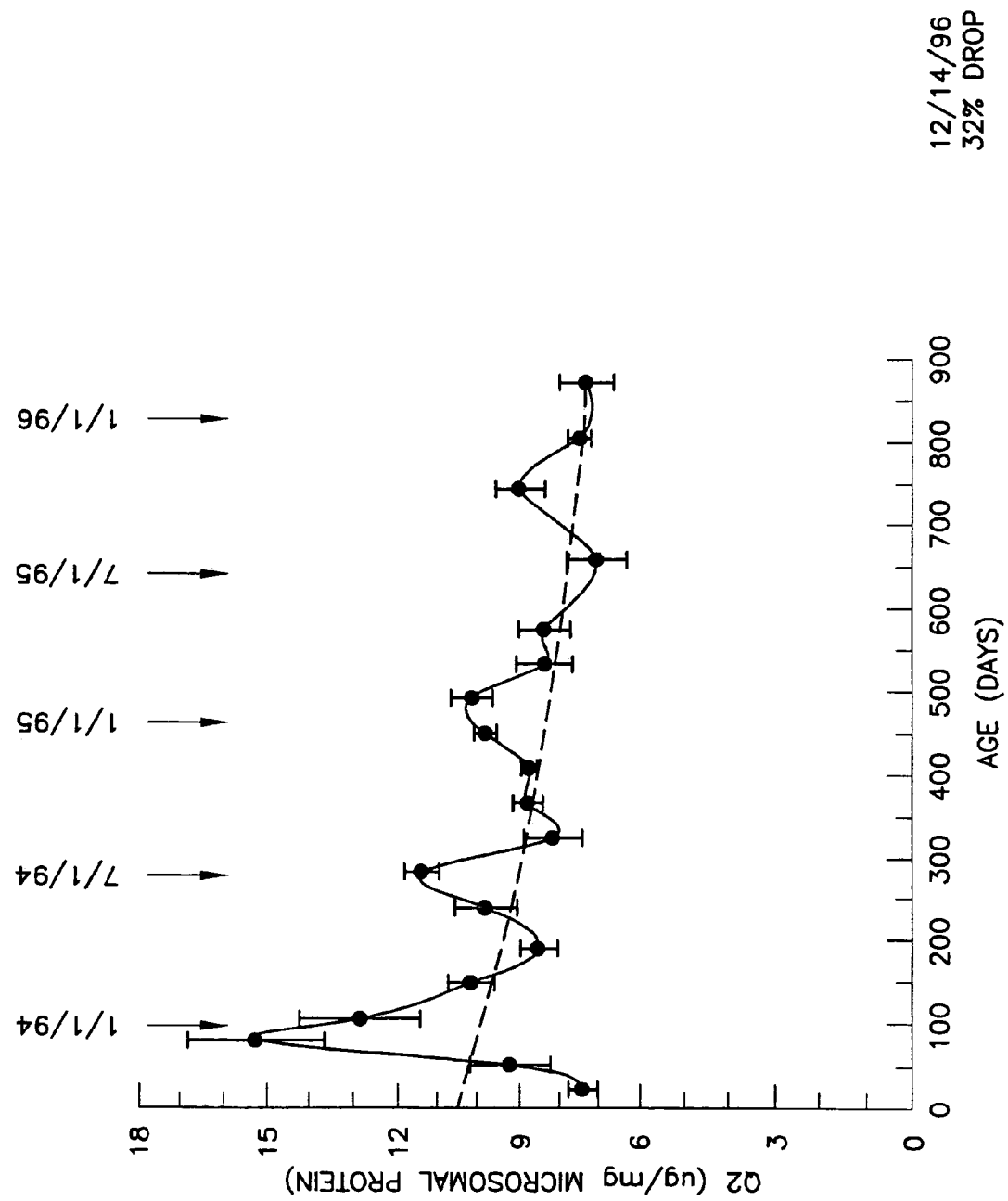
FIG. 8 illustrates rat hepatic, microsomal Q2 levels as a function of age.
Figure 9:
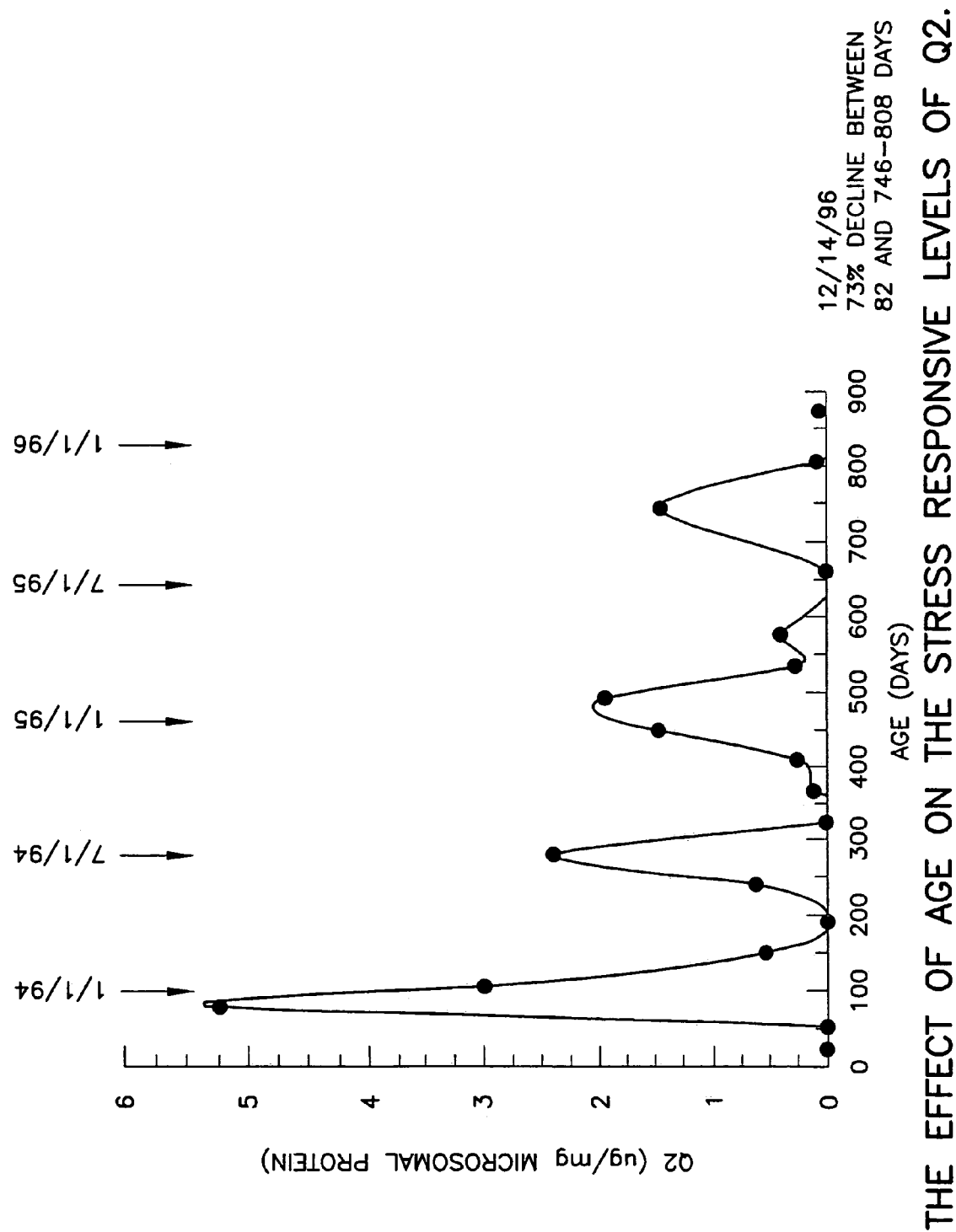
FIG. 9 illustrates rat stress-responsive levels of Q2 as a function of age.
Figure 10:
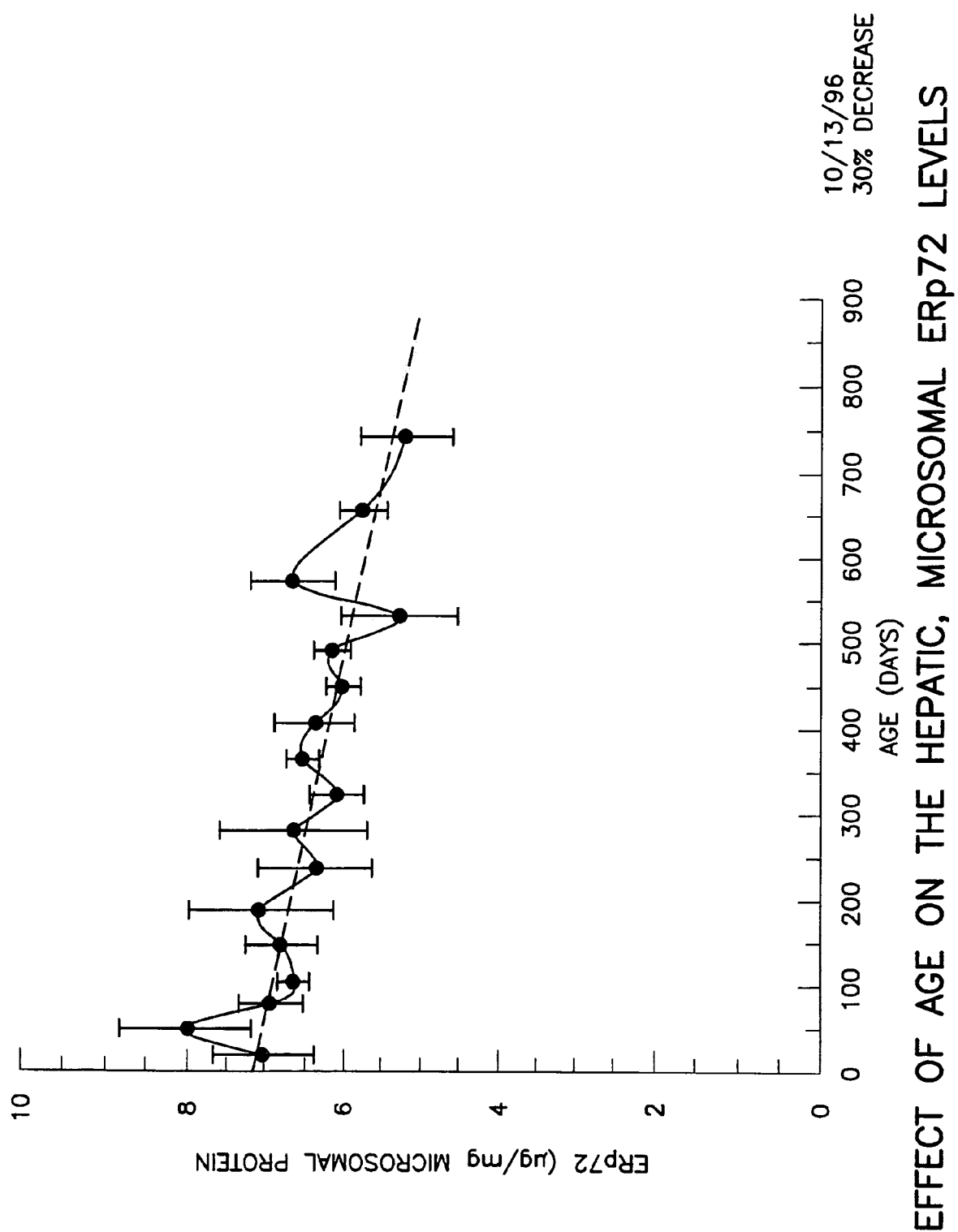
FIG. 10 illustrates rat hepatic, microsomal Erp72 levels as a function of age.

These studies yielded the results reported in Table 1 and in FIGS. 1–13. In particular, FIG. 6 shows a decline in Q5 concentration as a rat ages; FIG. 7 shows a decline in Q5 concentration for stress responsiveness as a rat ages; FIG. 8 shows a decline in Q2 concentration as a rat ages; FIG. 9 shows a decline in Q2 concentration for stress responsiveness as a rat ages; FIG. 10 shows a decline in ERp72 concentration as a rat ages.

Figure 11:
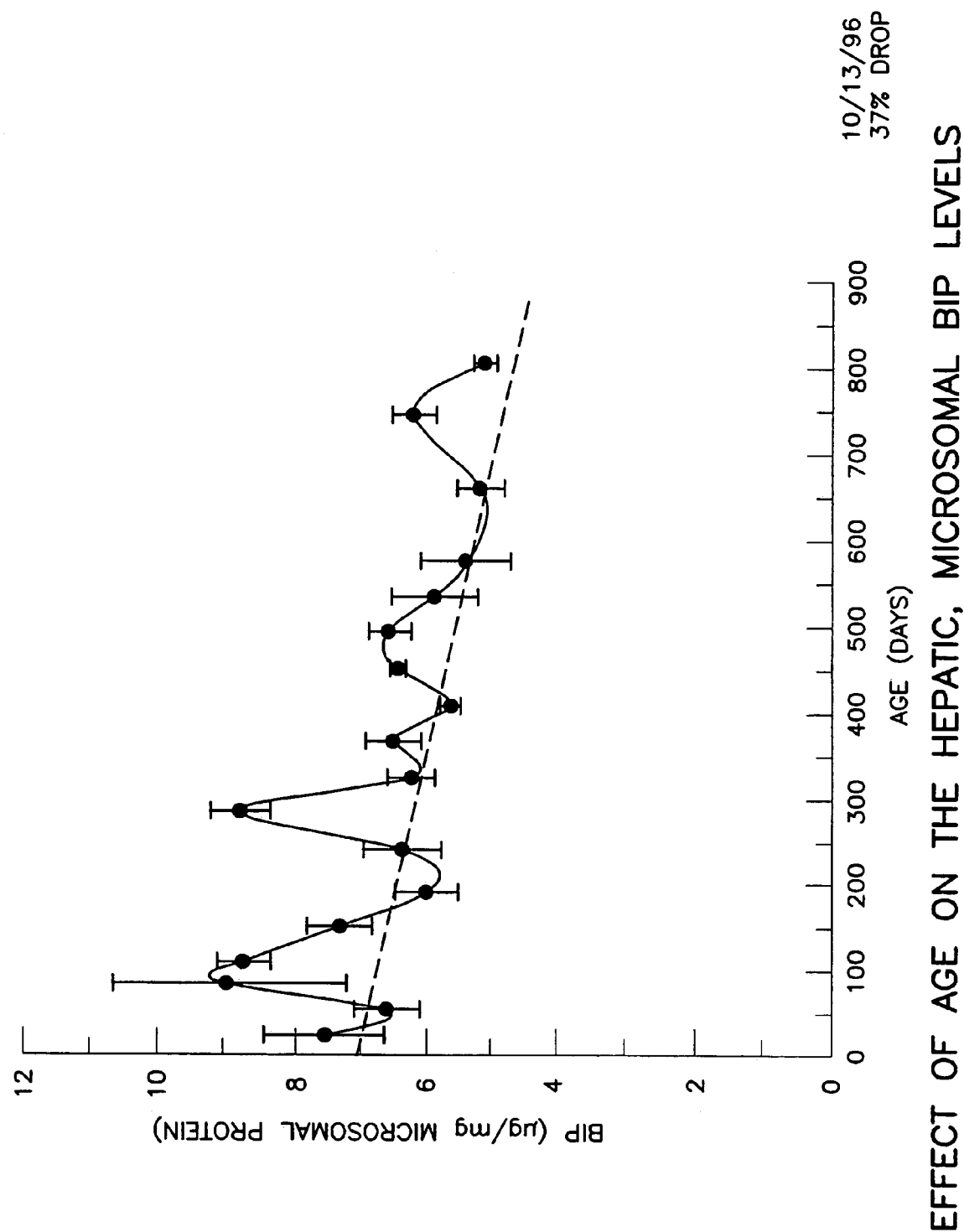
FIG. 11 illustrates rat hepatic, microsomal BiP levels as a function of age.
Figure 12:
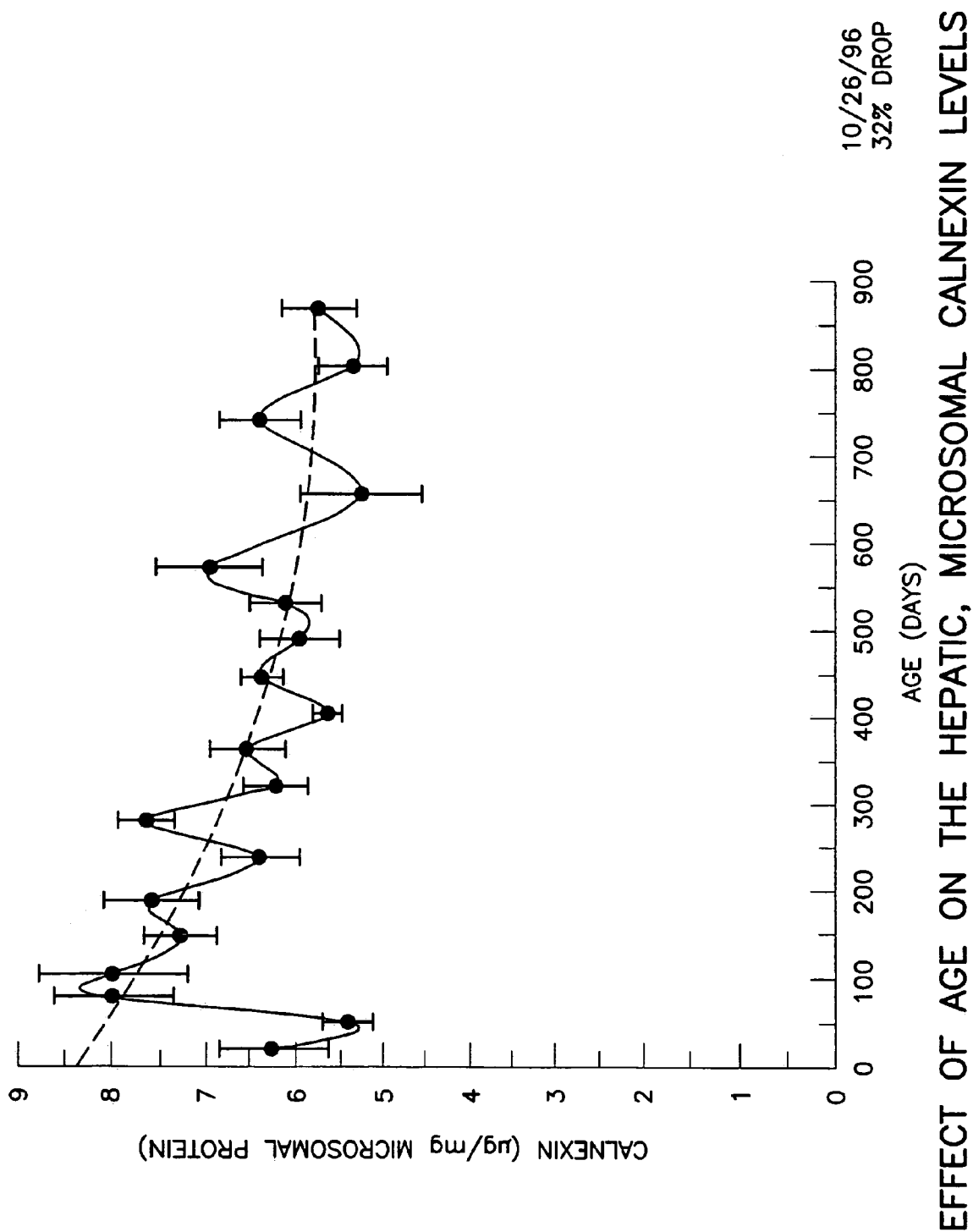
FIG. 12 illustrates rat hepatic, microsomal calnexin levels as a function of age.
Figure 13:
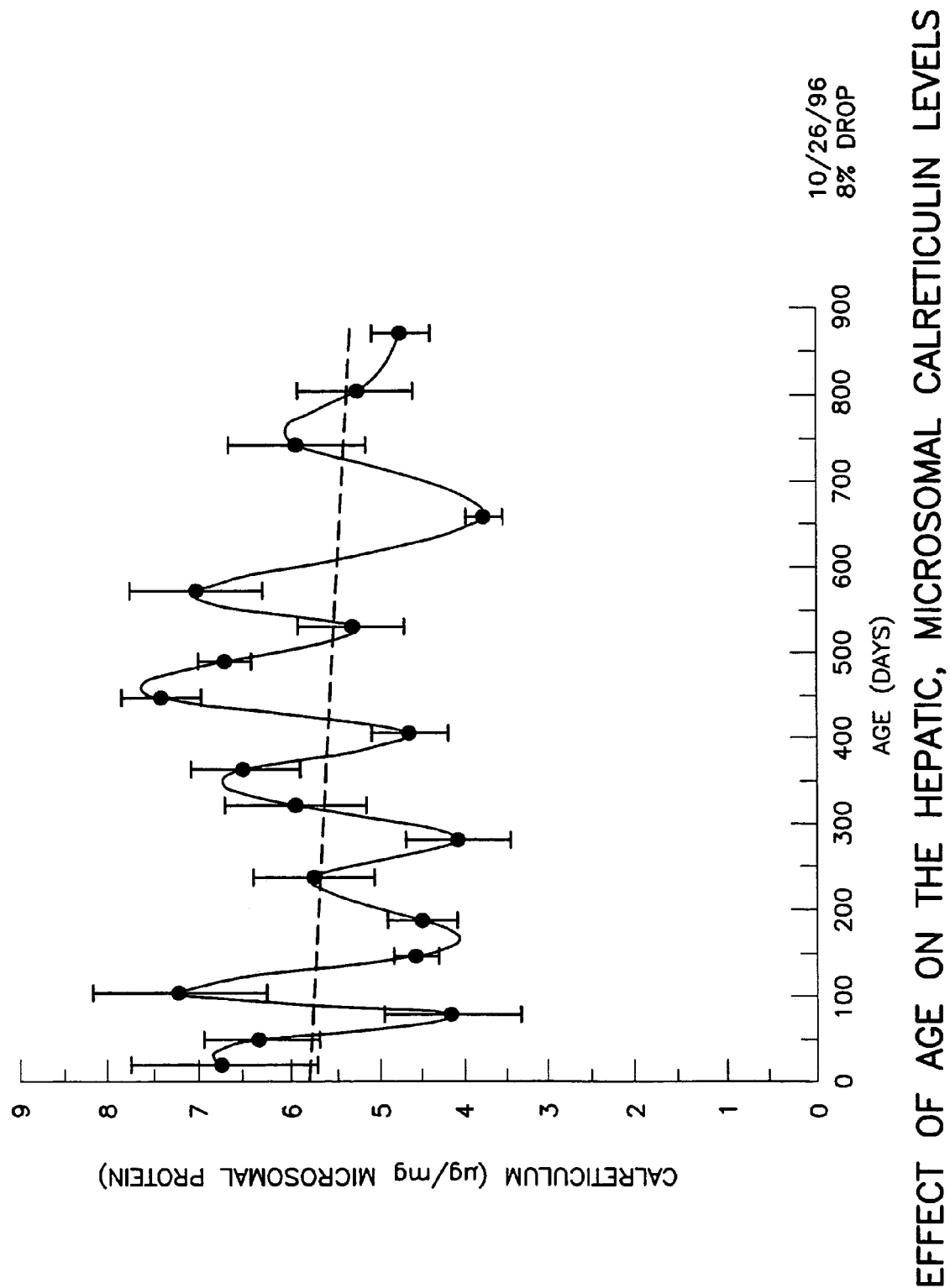
FIG. 13 illustrates rat hepatic, microsomal calreticulin levels as a function of age.

FIG. 11 shows a decline in BiP concentration as a rat ages; FIG. 12 shows a decline in calnexin concentration as a rat ages; and FIG. 13 shows no significant decline in calreticulin levels as a rat ages.

TABLE 1

Effect of Age and Stress on the Concentrations of the Various ER Chaperons.

| Chaperon | Peak Concentration µg/mg Prot | Concentration @ 874 days µg/mg Prot | Constitutive Decline % ($R^2$) | Show Stress Response | Stress Decline % |
|---|---|---|---|---|---|
| BiP | 80.0 | 48.5 | 39 (0.9586) | Yes | 50 |
| Calnexin | 57.4 | 40.5 | 29 (0.9398) | No | — |
| Calreticulin | 7.6 | 4.8 | 8 | No | — |
| ERp72 | 141 | 100 | 30 (0.8840) | No | — |
| Q2 | 15.4 | 8.2 | 32 (0.8414) | Yes | 71 |
| Q5 | 34.8 | 13.1 | 51 (0.8989) | Yes | 73 |
| Total | 336.2 | 215.1 | | | |

Discussion

The effect of aging on the microsomal content of the six chaperones showed markedly different patterns (FIGS. 6–13; Table 1). The most unusual patterns were seen with Q5 (FIG. 6; Table 1), Q2 (FIG. 8; Table 1), and BiP (appendix FIG. 11; Table 1). The constitutive levels of Q5 were highest in the youngest animals and showed a 51% decline as the animals reached maturity (Dotted line, FIG. 6). This pattern would be predicted for a constituent that is critical for growth and proliferation. Since on reaching maturity the hepatocytes enter into a Go phase, these cells have far less demand for new membrane components. Hence, it would be expected, as observed, that a chaperon involved in membrane synthesis would show significant decreases. After the age of 200 days the Q5 content showed a slower, but steady, decline. Q5 also showed a marked seasonal variation, having peaks that coincided with midwinter and midsummer. (FIG. 6). This is illustrated more clearly when the constitutive levels are subtracted and the remainder replotted (FIG. 7).

The rhythm coincides with the most stressful seasons of the year. Thus, cyclic variation indicates "stress responsiveness" of the respective chaperone. This stress arose from humidity changes, which range between 30 and 70% during the year. The initial peak in the first winter is markedly blunted compared to the following summer, resulting from the very high constitutive levels observed until the age of 200 days (FIG. 6). Hence, the cells were already producing almost maximal quantities of the respective chaperon. The constitutive levels declined in later ages, but the animals still showed a marked stress response (FIG. 7). As has been suggested by other studies, the stress response decreased with age, showing a 73% decline by 874 days.

Q2 showed a pattern similar to Q5, except for constitutive levels. Q2 content showed increasing constitutive levels as the animals reached maturity and then showed a 32% decline between the ages of 84 days and 874 days. (FIG. 8). The levels also showed a stress response. When the constitutive levels are subtracted out, the levels have a circum semiannual rhythm. These peaks also correspond to mid-winter and midsummer. (FIG. 9). This stress response showed a 71% decline with age.

The changes in the ratio of the constitutive levels of Q2 to Q5 corresponding to age is important. Q5 catalyzes the configuration of nascent and denatured proteins into their native tertiary structure and the formation of disulfide bonds. Additionally, although it is not a transferase, Q5 also is required for the N-glycosylation of membrane and secretory proteins. Recent studies indicated that Q2 is involved in the insertion of N-glycosylated proteins into the membrane. The peak demand for the insertion of N-glycosylated proteins into the membrane is at an early age when the animals are rapidly growing. After the liver reaches its mature weight, the cell would have much less need under constant environmental conditions for high levels of proteins that help with insertion because the cells are no longer growing or proliferating. Thus, Q2 is not the primary chaperon in the hepatocyte, at least in young animals.

Unlike Q2 and Q5, ERp72 showed no seasonal variation. However, similar to Q5, the young animals had the highest concentrations and showed a 30% decline with age. (FIG. 10; Table 1). Although the exact function of ERp72 has not been clearly defined, it is known to be a chaperon and is one of the most highly conserved proteins in the animal kingdom. Human ERp72 reportedly is identical to the nematode, *Caenorhabditis elegans*. Any such highly conserved protein likely serves a critical role in cellular metabolism. Presumably, this relates to its chaperon activity.

BiP is a member of the HSP 70 family believed to serve primarily as a scavenger of improperly edited proteins. BiP showed a pattern similar to Q2 and Q5 (FIG. 11), having a 37% decline with age and some seasonal variation.

Unlike all of the above-described chaperones, calreticulin (a chaperone critical for cell function) showed no significant decline with age. (FIG. 12). Yet its membrane bound homolog, calnexin, showed a marked decline but no seasonal variation (FIG. 13). Furthermore, like Q2, calnexin had low concentrations in young animals, reached a peak at 84 days, and then declined 32% by the age of 874 days. The role of this chaperon in protein synthesis has been extensively studied and is critical to the synthesis of both membrane and secretory proteins.

CONCLUSION

Since the above data are reported per milligram microsomal protein, it is clear that all of them, with the exception of calreticulin, showed marked, statistically significant declines in specific content with age (30–50%) ($R^2=0.9586$ to 0.8414). (i.e. these proteins were declining out of proportion to the other proteins in the hepatic ER). Furthermore, this decline occurred in an organ, the liver, whose function is thought to remain relatively well-conserved with age. Unlike the CNS, immune system, endocrine organs, or kidneys, the liver neither loses weight nor overtly loses of function. For example, the serum levels of the primary secretory protein produced by the liver, albumin, does not decline with age, in spite of a clear loss of protein synthetic capacity.

Example 2

Identification of a Chaperone in Human Cerebrospinal Fluid

Chaperones form soluble complexes with a wide variety of secretory proteins. Since the animal study of chaperones in the hepatic microsomes showed a decline in level of some chaperones as the animals aged, it is important to determine whether any of these chaperones are associated with human cerebrospinal fluid and whether they play a role in Alzheimer's disease.

Materials and Methods

Cerebrospinal fluid samples were clinical waste provided by the Anesthesia Service of the VAMC and the Laboratory Service, Regions Medical Center, St. Paul, Minn. from normal, healthy patients who were subjected to a spinal tap for spinal anesthesia or to test for meningitis. The patients from whom cerebrospinal fluid samples were taken included 3 infants, 1 young adult, and 4 elderly patients.

The cerebrospinal fluid was examined for the presence of six chaperones: ERp72, calnexin, calreticulin, BiP, Q2, and thiol:protein disulfide oxidoreductase of the form Q5 (Q5). ERp72, calreticulin, calnexin Q2, and Q5 were prepared by methods known in the art. Srivastava et al., *J. Biol. Chem.,* 265: 8392–99 (1991); Chen et al., *Biochemistry,* 25: 8299–8306 (1996).

The chaperone content was determined by immunoblotting the preparations according to the methods described in Example 1. The concentration of chaperone was determined by comparison of various concentrations to the average density of three channels on each gel containing a reference sample of cerebrospinal fluid. The cerebrospinal fluid standards were calibrated against several concentrations of the standard cerebrospinal fluid. The determinations of the proteins in the cerebrospinal fluid were all within the linear range of the immunoassays. Polyclonal antibodies to all chaperones were developed or obtained according to the methods of Example 1.

The immunoblot was also incubated with antibodies to β-amyloid 1–42 (AMY-33; zymed, South San Francisco, Calif.).

Results

Only Q2 was identified in human cerebrospinal fluid. The levels of other chaperones, if present, were undetectable. Q2 showed a diffuse band corresponding to a molecular weight of approximately 62 kDa (FIG. 14A, lanes 3–7 and 9–14). Human cerebrospinal fluid was compared to rat hepatic microsomes. The rat microsomes showed a sharp band corresponding to a molecular weight of approximately 57 kDa (FIG. 14A, lane 2). Similarly, purified Q2 showed a sharp band corresponding to a molecular weight of 57 kDa (FIG. 14A, lane 8). The identity of Q2 was confirmed with rabbit monoclonal antibodies to Q2 (GRP58, StressGen, Vancouver, B.C.) (not shown).

The antibodies to β-amyloid 1–42 reacted with rat hepatic microsomes (FIG. 14B, lane 2), but they did not react with purified Q2 (FIG. 14B, lane 8).

Discussion

Because the reaction of β-amyloid 1–42 antibodies with rat, hepatic microsomes and the reaction of antibodies to Q2 with rat hepatic microsomes showed similar bands at molecular weights that correspond to about 57 kDa, this suggests β-amyloid and Q2 form a complex in the liver. Moreover, because β-amyloid 1–42 antibodies did not react with purified Q2, the results do not arise from cross reactivity.

Although the immunoblot incubated with Q2 antibodies and the immunoblot incubated with β-amyloid 1–42 antibodies showed different patterns, the patterns were still similar. This would suggest that the two are present in cerebrospinal fluid as a tight complex.

CONCLUSION

The chaperone Q2 is present in human cerebrospinal fluid.

Example 3

Isolation of a Complex of Q2 with β-Amyloid from Human Cerebrospinal Fluid

A complex of Q2 and β-amyloid was discovered and isolated from human cerebrospinal fluid, leading to a better understanding of the role of Q2 in human cerebrospinal fluid and Alzheimer's disease.

Materials and Methods

An immunoblot was prepared according to Example 1 to examine the 62 kD band observed in human cerebrospinal fluid. The immunoblot was incubated with a polyclonal antibody to Q2 and a second immunoblot was incubated with monoclonal antibodies to β-amyloid 1–42 (AMY-33 from Zymed, South San Francisco, Calif.). A diffuse band was identified again at 62 kDa for cerebrospinal fluid. The band for the monomeric form of β-amyloid 1–42 corresponded to a molecular weight of 5.5 kDa.

Q2: β-amyloid complex was isolated by affinity chromatography using chicken-anti-β-amyloid antibody. Alternatively, isolation by affinity chromatography was accomplished with anti-Q2. The complex was identified by immunoblotting as described in Example 1. The complex was further purified by chromatography on a Sephacryl column followed by a monoQ column.

Polyclonal antibodies to a purified sample of Q2 were developed in laying hens as described in Example 1. Synthetic β-amyloid 1–42 antibodies also were prepared in chickens by the same method.

Cerebrospinal fluid samples eluted from affinity chromatography with chicken-anti-β-amyloid and, alternatively, from affinity chromatography with anti-Q 2, were examined by immunoblot. The chicken antibodies to Q2 and β-amyloid were bound to CNBr-activated Sepharose. The cerebrospinal fluid sample was placed on the column in NaCl (1M). The column was washed and the protein eluted with glycine (0.1M, pH 9.0) in NaCl.

Immunoblots were performed after SDS-PAGE and transblotting onto PVDF membranes. Srivastava, *J. Biol. Chem.*, 266: 20337–20344 (1991); Chen et al., *Biochemistry* 25: 8299–8306 (1996); Towbin et al., *Proc. Natl. Acad. Sci. USA*, 76: 4350–54 (1979). The samples were heated to 55° C. for 5 minutes in the presence of mercaptoethanol. If they were heated to 90° C., the complex aggregated and no bands were observed. The bands were reacted with the appropriate goat anti-immunoglobulin antibody coupled to alkaline phosphatase. The indicator dye was a combination of nitroblue tetrazolium and 5-bromo-4-chloro-3-indoyl phosphate (BioRad, Richmond, Calif.). The band intensity was quantitated by computer scanning and analysis (NIH Image Version 1.60).

Results

Figure 15:
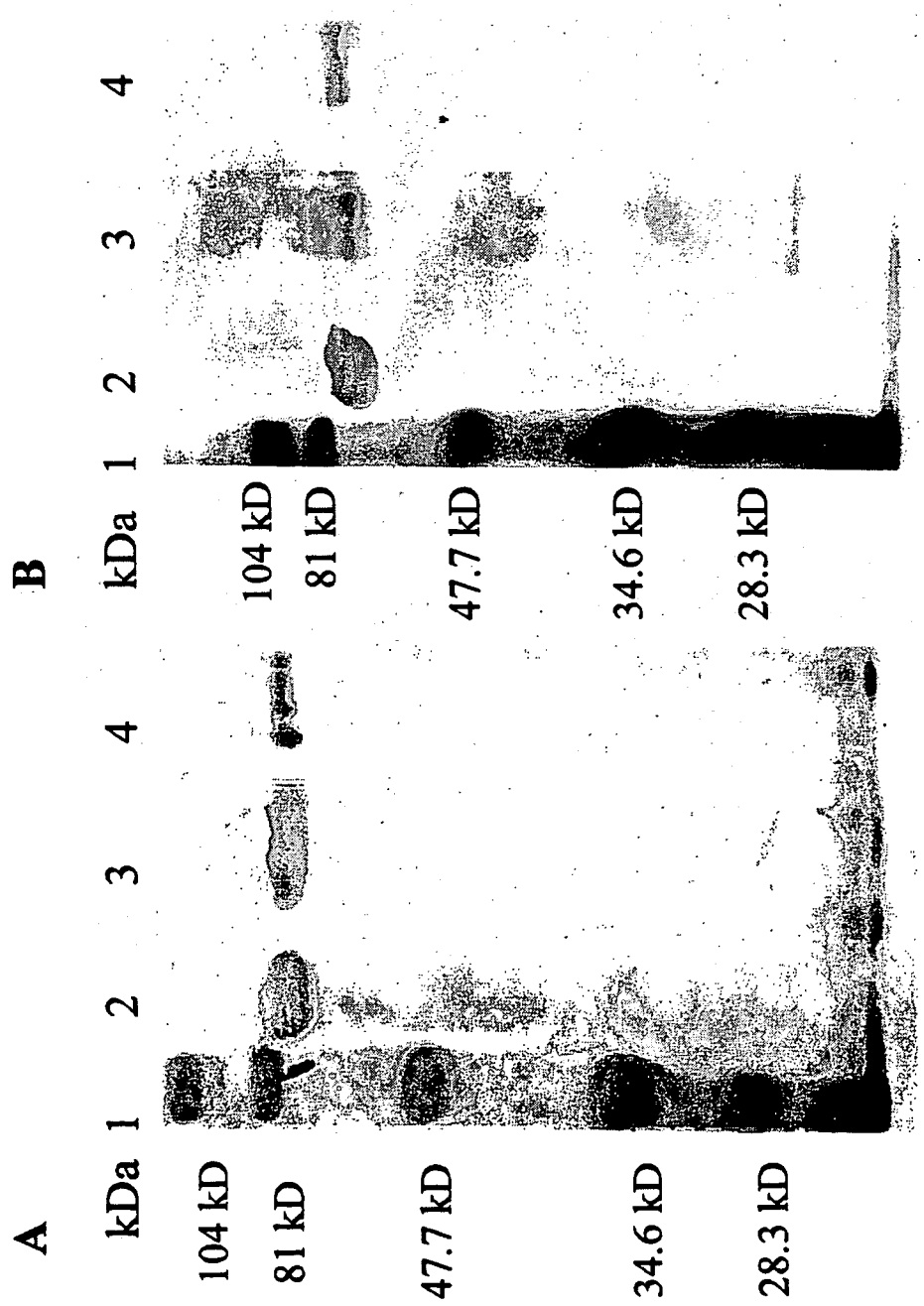
FIG. 15A illustrates another immunoblot of biological samples with polyclonal antibodies to Q2.
FIG. 15B illustrates another immunoblot of biological samples with polyclonal antibodies to $\beta$-amyloid 1–42.

Blots incubated with antibodies to Q2 showed diffuse bands corresponding to a molecular weight of approximately 62 kDa (FIG. 15A, lanes 3 and 4). Similar bands also were detected when blots were incubated with antibodies to β-amyloid 1–42 (FIG. 15B, lanes 3 and 4). Additionally, the anti-β-amyloid 1–42 was shown not to be reactive to Q2.

Blots incubated with antibodies to β-amyloid 1–42 also revealed a band corresponding to a molecular weight of approximately 62 kDa. But β-amyloid has a molecular of about 5.5 kDa. In addition to the 62 kDa band identified on the immunoblots, a 27 kDa band was identified when incubated with anti-β-amyloid 1–42 (FIG. 15B, lane 3). This 27 kDa band was also observed when synthetic β-amyloid 1–42 was stored at −20° for several weeks and then run on a gel and, therefore, represents a β-amyloid 1–42 pentamer.

Monoclonal β-amyloid antibody (AMY-33) is highly specific for β-amyloid and is known to bind only to bind to fibrinogen outside of β-amyloid. Stern et al., *FEBS Let.*, 245: 43–47 (1990). But the molecular weight bands observed in this study were different from those observed with fibrinogen. Moreover, anti-fibrinogen antibodies did not react with any protein in cerebrospinal fluid.

Scanning the blots indicated that 95% of the immunoreactive β-amyloid was associated with the 62 kDa band, whereas 5% was associated with bands of lower molecular weight. This corresponds to a high binding affinity.

These results were confirmed in 100 additional cerebrospinal fluid samples. The same pattern of immunoreactive bands to Q2 and β-amyloid were observed for all 100 samples.

Discussion

Most groups that have examined the effect of Alzheimer's disease on the cerebrospinal fluid concentrations of β-amyloid have used a variety of ELISAs or similar assays, but five have performed immunoblot studies and each observed markedly different results. One study observed only low Mr immunoreactive bands. Ida et al., *J. Biol. Chem.*, 271: 22908–22914 (1996). Yet the present study showed that 95% of the immunoreactive β-amyloid 1–42 corresponded to a molecular weight of 62 kDa and only 5% with the lower molecular weight. The other groups apparently used more highly denaturing conditions in the preparation of their samples than those used in this study, presumably dissociating the complex. In the present study the complex was not dissociated.

Other studies may have observed different immunoreactive bands because the antibodies may have differed in specificity from those used here. Seubert et al., *Nature*, 361: 260–63 (1993); Globek et al., *Neurosci. Let.*, 191: 79–82 (1995).

In a study of the interaction of β-amyloid with high density lipoproteins, an immunoreactive band at 62 kDa was observed (Koudinov et al, *Biochem. Biophys. Res. Commun.*, 223: 592–97 (1996); Ghiso et al., *Biochem. J.*, 293: 27–30 (1993)), but soluble β-amyloid from the fraction that produced a 62 kDa band was not retrieved and the fraction that produced the 62 kDa band was not identified or characterized.

The band corresponding to a molecular weight of 62 kDa would be indicative of a complex between β-amyloid 1–42 and Q2. Because this band was diffuse, this suggests that the complex between β-amyloid 1–42 and Q2 is glycosylated.

CONCLUSION

A complex of Q2 and β-amyloid 1–42 was found in human cerebrospinal fluid. By binding to β-amyloid 1–42, Q2 keeps β-amyloid 1–42 in solution and helps prevent aggregation and precipitation of β-amyloid.

Example 4

Characterization of a Complex of Q2 with β-Amyloid 1–42

The complex of Q2 and β-amyloid was characterized to better understand the role of this complex in preventing formation of β-amyloid plaques and in Alzheimer's disease.

Materials and Methods

A complex of Q2 with β-amyloid was purified as described in Example 3.

The presence of carbohydrate moieties on the complex was determined by methods known to those of skill in the art. In particular, the complex was reacted with PAS. The PAS-reacted complex was eluted through a boronate column.

Results

When the complex was reacted with PAS, a band corresponding to a molecular weight of 62 kDa was identified. Moreover, the PAS-reacted complex bound to a boronate column, which suggests the presence of a carbohydrate moiety.

Discussion

The results from the reaction of the complex with PAS are consistent with the observation of the diffuse band corresponding to a molecular weight of 62 kDa described in Example 3. These results are also consistent with other studies that have indicated that Q2 has lectin-like properties and that Q2 may bind to proteins only after being N-glycosylated. Oliver et al., Science, 275: 86–88 (1997); Elliott et al., J. Biol. Chem., 272: 13849–13855 (1997). N-glycosylation may be important in the post-translational processing of many proteins that are synthesized in the endoplasmic reticulum. Suzuki et al., J. Biol. Chem., 272: 10083–10086 (1998).

The likelihood that the complex is N-glycosylated is also supported by the observation that the complex was relatively stable under the moderately severe denaturing conditions that were used to solubilize the samples for the SDS-Page and immunoblot analyses.

CONCLUSION

Although Q2 and β-amyloid have not been shown to be glycosylated when not in complex, these results suggest that Q2: β-amyloid is glycosylated as a complex.

Example 5

Detection of β-Amyloid Plaques and Correlation of Plaque Presence to Q2 Levels and/or apoE Genotype As Q2 levels decline relative to normal Q2 levels, a person can have an increased susceptibility to, for example, β-amyloid aggregation, having Alzheimer's disease, having symptoms associated with Alzheimer's disease, or likelihood of developing Alzheimer's disease. It is desirable to understand this correlation.

Methods and Materials

Cerebrospinal fluid samples and brain samples were taken from autopsy specimens. The specimens were obtained from 21 nuns who participated in a study in which their health status and psychomotor abilities were evaluated and monitored until their deaths. Snowdon, JAMA, 277: 813–17 (1997). The cerebral spinal fluid samples were frozen at the time of collection and stored at $-70°$ C.

The cerebrospinal fluid samples were examined for the presence of chaperones as described in Example 1 with some modifications. Immunoblots were performed after SDS-PAGE and transblotting onto nitrocellulose membranes. Laemmli, Nature, 227: 680–85 (1970); Towbin et al., Proc. Natl. Acad. Sci. USA, 76: 4350–54(1979). The samples were heated to 55° C. for 5 minutes in the presence of SDS and mercaptoethanol. If they were heated to 90° C., the complexes aggregated and no bands were observed. In a first study, the bands were reacted with antibodies specific for the molecule of interest and then with the appropriate goat anti-immunoglobulin antibodies coupled to alkaline phosphatase. The antibodies specific for the molecule of interest were polyclonal antibodies to calmodulin, calnexin, BiP, ERp72, Q2, Q5, and synthetic β-amyloid 1–42. Antibodies to BiP and Q2 were purchased from StressGen (Vancouver, B.C.). Antibodies to β-amyloid 1–42 were purchased from Zymed (AMY-33; South San Francisco, Calif.). All other antibodies were prepared in laying hens as described in Example 1. The indicator dye used was a combination of nitroblue tetrazolium and 5-bromo-4-chloro-3-indolyl phosphate (BioRad, Richmond, Calif.).

In a second study, cerebrospinal fluid samples eluted from affinity chromatography with anti-Q2 and, alternatively, anti-β-amyloid 1–42, were examined by immunoblot. The antibodies were first bound to CNBr-activated Sepharose. The resin was suspended in NaCl (1M), mixed with 1 ml CSF sample, incubated overnight at 4° C., and then poured into a column. The column was washed with NaCl until the eluate had no absorbance at 280 nm. The bound proteins were eluted with glycine (0.1 M, pH 9.0) in NaCl. Q2 and β-amyloid 1–42 were identified according to the immunoblotting procedure described above.

In a third study, the concentration of Q2 was determined from the immunoblots by enhanced chemiluminescence with a peroxidase reaction (RPN 2106; Amersham Life Science, Piscataway, N.J.). The band intensities were quantitated by computer scanning of the chemiluminescence photographic film and analyzed by NIH Image (Version 1.60).

The brain samples obtained from the nuns were examined to determine the total number of β-amyloid plaques, including both diffuse and neuritic types of plaque. The total plaque numbers were determined from the five most severely affected microscopic fields of Bielschoasky-stained sections of the frontal, temporal, and parietal lobes of the neocortex.

The brain samples obtained from the nuns were also examined to determine the apoE genotype of the subject. Snowdon et al., J. Am. Med. Assoc., 277: 813–17 (1997).

Results

The chemiluminescence assay was linear with concentrations of Q2 between about 5 and 45 ng/ml of cerebrospinal fluid.

FIG. 16 and Table 2 show a significant correlation between the concentration of Q2 and the total number of plaques ($r=-0.52$, $p<0.02$, 95% CI–0.25 to –0.79 by the Spearman rank correlation test).

Discussion

The cerebrospinal fluid samples from the nuns showed three distinct groups. The first had an abundant number of plaques and less than 17 ng/ml of Q2 (6 of 21). The second group had normal levels of Q2 and an abundant number of plaques (8 of 21). The third group had little or no plaques and normal levels of Q2. But the third group is the only group that showed only apoE$_2$ or apoE$_3$ alleles (Table 2).

TABLE 2

Ventricular Cerebrospinal Fluid Q2 Concentrations, Senile Plaque Scores, Apolipoprotein E Genotype and Age of the Autopsied Participants in the Nun Study.

| Group | CSF Q2 ng/ml | Senile Plaque Scores | ApoE Genotype | Age Years |
|---|---|---|---|---|
| Low Q2 and Abundant Senile Plaque | 6.9 | 21.1 | 3,3 | 79 |
| | 14.3 | 21.3 | 3,3 | 94 |
| | 14.8 | 21.3 | 4,4 | 81 |
| | 15.5 | 21.3 | 3,3 | 86 |
| | 16.3 | 21.3 | 2,3 | 93 |
| | 16.9 | 21.3 | 3,3 | 84 |
| | | | | Average age 86.2 ± 2.3 |
| Normal Q2 and Abundant Senile Plaque | 17.1 | 21.3 | 3,4 | 89 |
| | 17.8 | 21.3 | 3,4 | 83 |
| | 23.8 | 20.8 | 3,4 | 88 |
| | 25.3 | 21.3 | 4,4 | 85 |
| | 26.7 | 20.8 | 3,3 | 91 |
| | 29.0 | 21.3 | 3,4 | 80 |
| | 32.1 | 20.8 | 3,3 | 96 |
| | 33.6 | 21.0 | 3,3 | 92 |
| | | | | Average age 88.0 ± 1.7 |
| Normal Q2 and Little or No Senile | 17.8 | 4.1 | 3,3 | 81 |
| | 21.0 | 4.9 | 3,3 | 83 |
| | 22.1 | 0.0 | 3,3 | 82 |
| | 22.2 | 0.0 | 3,3 | 86 |
| | 25.4 | 0.0 | 2,3 | 92 |
| | 31.6 | 0.0 | 2,3 | 97 |
| | 31.9 | 0.0 | 2,2 | 90 |
| | | | | Average age 87.3 ± 2.1 |

As described in Example 3, about 5% of β-amyloid 1–42 is free in solution in normal subjects. Some studies have shown that apoE$_4$ more readily forms in soluble complexes with β-amyloid than do other isoforms of the apolipoprotein. Moir et al., *Biochemistry*, 38: 4595–4603 (1999). The results shown in Table 2 suggest that individuals having an apoE$_4$ genotype may form plaques at lower concentrations of free β-amyloid than do the other genotypes.

The data shown in FIG. 16 and Table 2 show that a person who does not have apoE$_4$ genotype and has normal Q2 levels has no or few plaques. Yet a person with low levels of Q2 has increased susceptibility to an abundant amount of plaques, irrespective of apoE genotype. That is, 100% of the people studied who showed a decline in Q2 levels relative to normal had an abundant amount of plaque. A person with normal levels of Q2 but with an apoE$_4$ allele also has increased susceptibility to an abundant amount of plaques. It should be noted, however, that only half of the people having normal levels of Q2 and an abundant amount of plaques had an apoE$_4$ allele. Thus, a third gene or protein may also be involved in the development of Alzheimer's disease.

The specimens from the nuns were also compared to specimens from 12 young people (3 to 16 years of age) and from 12 elderly people without Alzheimer's disease (66 to 82 years of age). The Q2 levels from the young subjects (27.3±1.2 ng/ml) and the elderly subjects (29.9±1.6 ng/ml) were the same as the Q2 levels observed in the nuns who had little or no senile plaques (24.6±1.9 ng/ml).

CONCLUSION

This study demonstrates an increased incidence of Alzheimer's disease in individuals with at least one apoE$_4$ allele and in individuals with Q2 levels less than 17 ng/ml, independent of apoE$_4$ genotype.

This invention has been described with reference to various specific and preferred embodiments and techniques. However, it should be understood that many variations and modifications may be made while remaining within the spirit and scope of the invention.

All publications and patent applications in this specification are indicative of the level of ordinary skill in the art to which this invention pertains.

What is claimed is:

1. An isolated complex comprising human chaperone protein ERp57/GRp58; and human β-amyloid 1–42 or human β-amyloid 1–38.

2. The isolated complex of claim 1, wherein the complex is glycosylated.

* * * * *